US011801086B2

(12) United States Patent
Morisaki

(10) Patent No.: US 11,801,086 B2
(45) Date of Patent: Oct. 31, 2023

(54) GRASPING TREATMENT INSTRUMENT

(71) Applicant: OLYMPUS CORPORATION, Hachioji (JP)

(72) Inventor: Kazuhiro Morisaki, Yokohama (JP)

(73) Assignee: OLYMPUS CORPORATION, Tokyo (JP)

( * ) Notice: Subject to any disclaimer, the term of this patent is extended or adjusted under 35 U.S.C. 154(b) by 1300 days.

(21) Appl. No.: 16/246,119

(22) Filed: Jan. 11, 2019

(65) Prior Publication Data

US 2019/0142505 A1 May 16, 2019

Related U.S. Application Data

(63) Continuation of application No. PCT/JP2016/070720, filed on Jul. 13, 2016.

(51) Int. Cl.
*A61B 18/14* (2006.01)
*A61B 17/28* (2006.01)
(Continued)

(52) U.S. Cl.
CPC ........ *A61B 18/1445* (2013.01); *A61B 17/282* (2013.01); *A61B 17/320092* (2013.01);
(Continued)

(58) Field of Classification Search
CPC .............. A61B 18/1445; A61B 17/282; A61B 17/320092; A61B 18/085; A61B 18/1482;
(Continued)

(56) References Cited

U.S. PATENT DOCUMENTS 6,193,709 B1 * 2/2001 Miyawaki ...... A61B 17/320092
606/49
2004/0193199 A1 9/2004 Hashiguchi
(Continued)

FOREIGN PATENT DOCUMENTS

EP 2074959 A1 * 7/2009 ..... A61B 17/320092
JP 2004-209042 A 7/2004
(Continued)

OTHER PUBLICATIONS

Nov. 26, 2020 Office Action issued in Chinese Patent Application No. 201680087604.1.
(Continued)

*Primary Examiner* — Linda C Dvorak
*Assistant Examiner* — Mystee Nguyen Delgado
(74) *Attorney, Agent, or Firm* — Oliff PLC

(57) ABSTRACT

The grasping treatment instrument includes a jaw including first and second rims and a recess with a bottom surface, and a grasping member with a ridge. When the grasping member is positioned at a first position, a component of the ridge between a second rotary axis and a distal end of the ridge protrudes to the opposite side from the bottom surface of the recess with respect to the first and second rims. When the grasping member is positioned at a second position, a component of the ridge between the second rotary axis and a proximal end of the ridge protrudes to the opposite side from the bottom surface of the recess with respect to the first and second rims.

19 Claims, 18 Drawing Sheets

(51) Int. Cl.
*A61B 17/32* (2006.01)
*A61B 18/08* (2006.01)
*A61B 18/00* (2006.01)

(52) U.S. Cl.
CPC ........ *A61B 18/085* (2013.01); *A61B 18/1482* (2013.01); *A61B 2017/2825* (2013.01); *A61B 2017/320094* (2017.08); *A61B 2018/00077* (2013.01); *A61B 2018/00083* (2013.01); *A61B 2018/00273* (2013.01); *A61B 2018/00595* (2013.01); *A61B 2018/00994* (2013.01); *A61B 2018/146* (2013.01); *A61B 2018/1457* (2013.01)

(58) Field of Classification Search
CPC ........... A61B 2017/2825; A61B 2017/320094; A61B 2018/00077; A61B 2018/00083; A61B 2018/00273; A61B 2018/00595; A61B 2018/00994; A61B 2018/1457; A61B 2018/146
See application file for complete search history.

(56) References Cited

U.S. PATENT DOCUMENTS

| | | | | |
|---|---|---|---|---|
| 2007/0074807 | A1* | 4/2007 | Guerra | B29C 70/72 156/242 |
| 2010/0057084 | A1* | 3/2010 | Hanna | A61B 18/1445 606/51 |
| 2013/0172885 | A1 | 7/2013 | Ichikawa et al. | |
| 2013/0303949 | A1* | 11/2013 | Kawaguchi | A61B 17/282 601/2 |
| 2015/0018856 | A1* | 1/2015 | Poo | A61B 17/1285 606/158 |
| 2015/0297289 | A1 | 10/2015 | Hirai et al. | |
| 2017/0000556 | A1* | 1/2017 | Morisaki | A61B 18/1206 |
| 2017/0354456 | A1* | 12/2017 | Fiksen | A61B 17/29 |

FOREIGN PATENT DOCUMENTS

| | | | |
|---|---|---|---|
| JP | 2008-264565 A | | 11/2008 |
| JP | 2011200586 A | * | 10/2011 |
| JP | 2014-121618 A | | 7/2014 |
| JP | 2016-73729 A | | 5/2016 |
| WO | 2015/137139 A1 | | 9/2015 |
| WO | 2016/021291 A1 | | 2/2016 |

OTHER PUBLICATIONS

Sep. 13, 2016 International Search Report issued in International Patent Application PCT/JP2016/070720.

Jan. 15, 2019 International Preliminary Report on Patentability issued in International Patent Application PCT/JP2016/070720.

Nov. 12, 2019 Office Action issued in Japanese Patent Application No. 2018-527315.

* cited by examiner

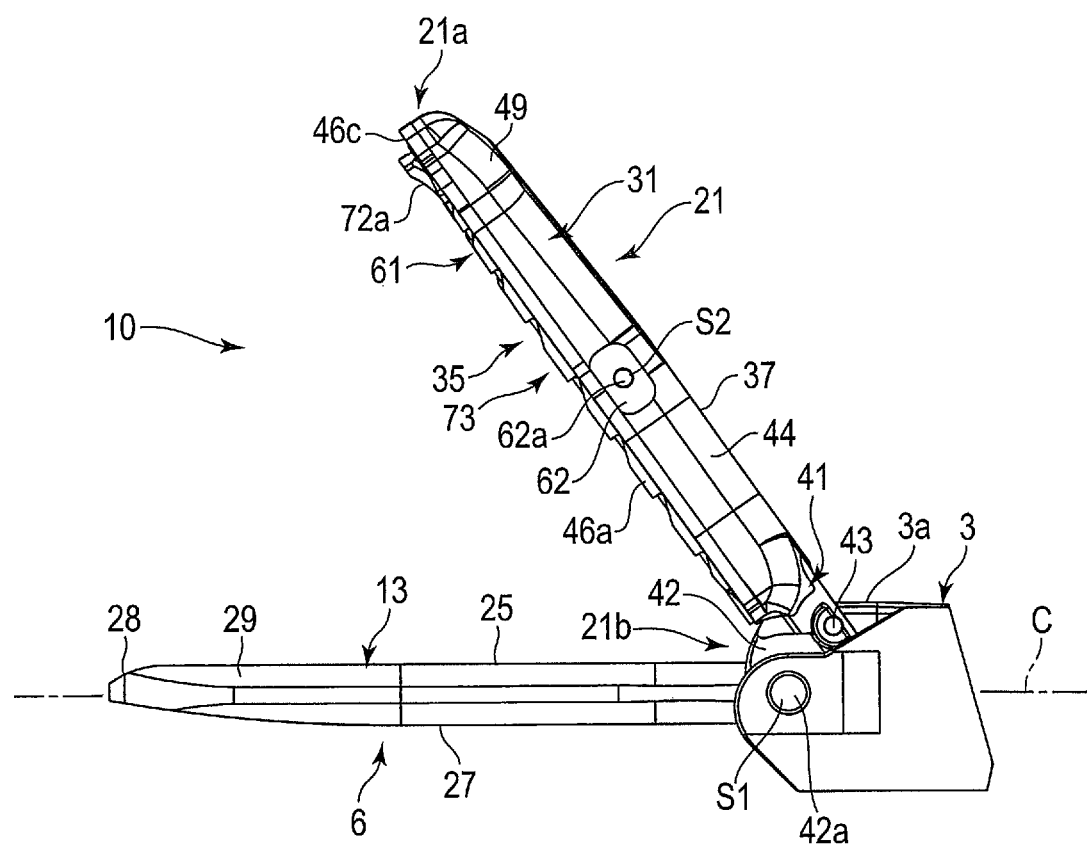
F I G. 2

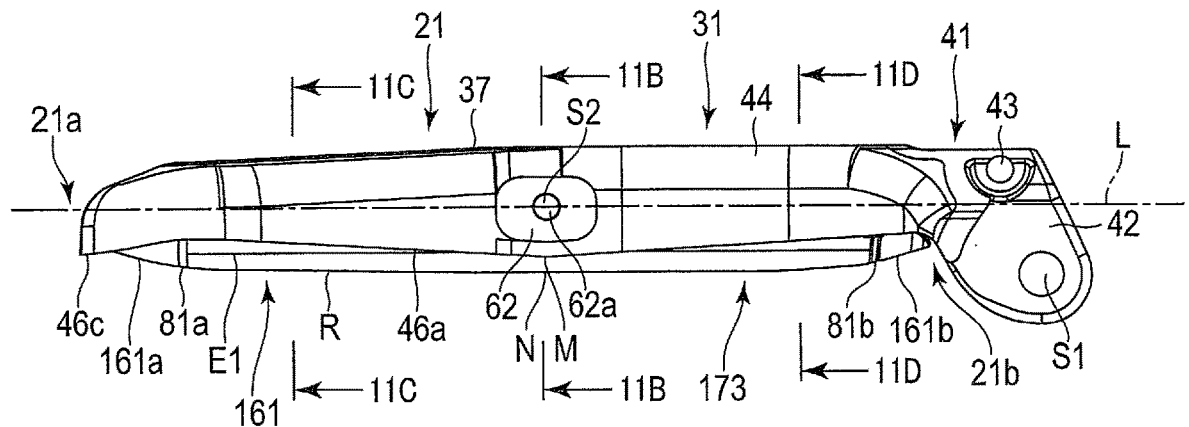
F I G. 11A
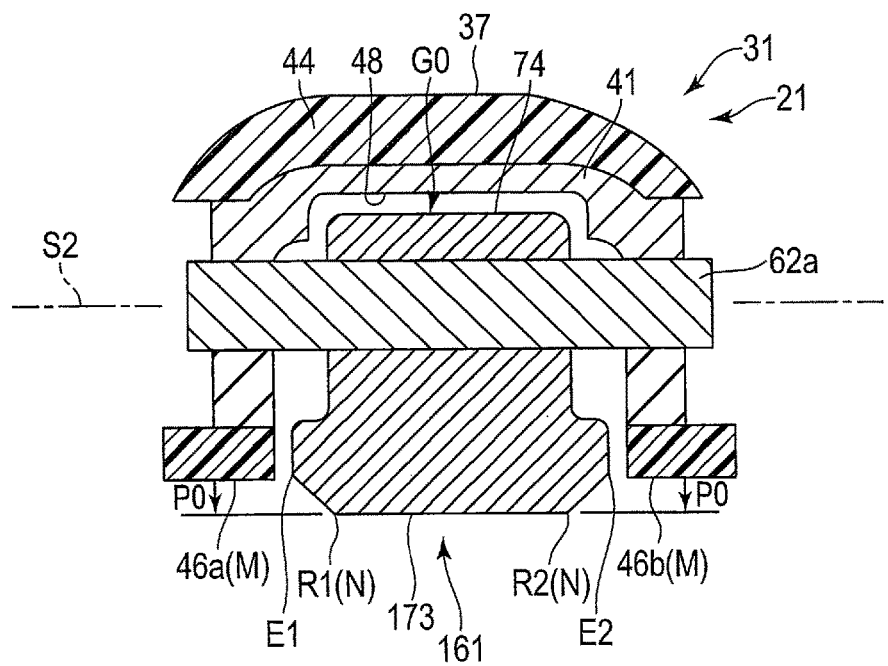
F I G. 11B

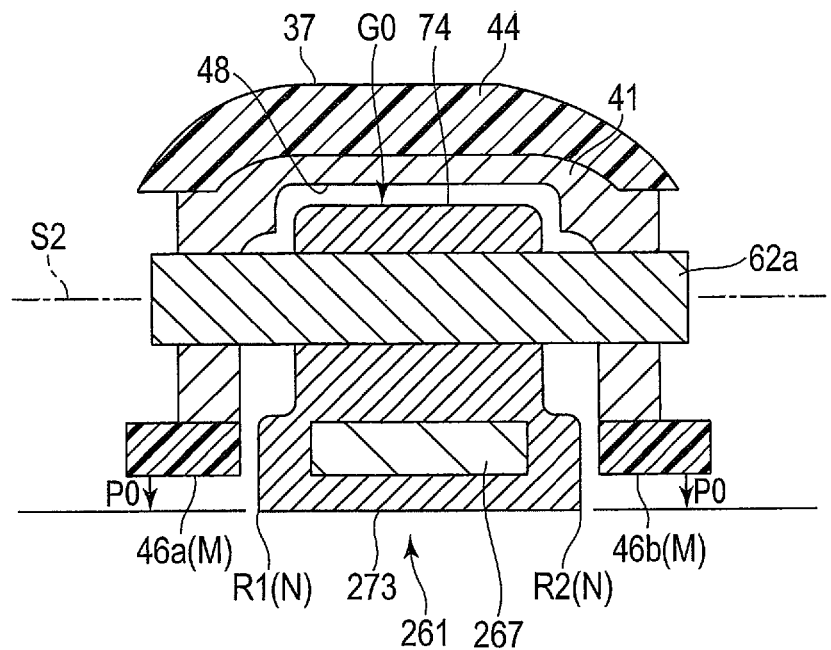
F I G. 14B
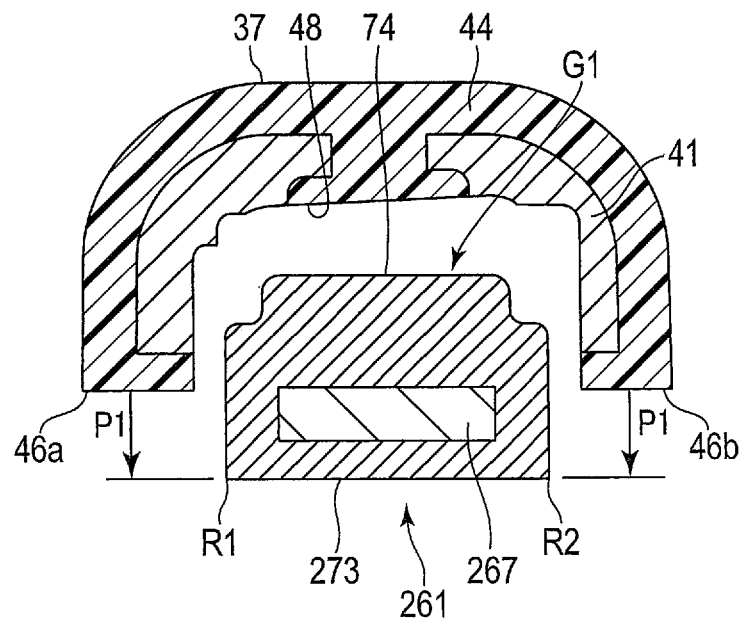
F I G. 14C

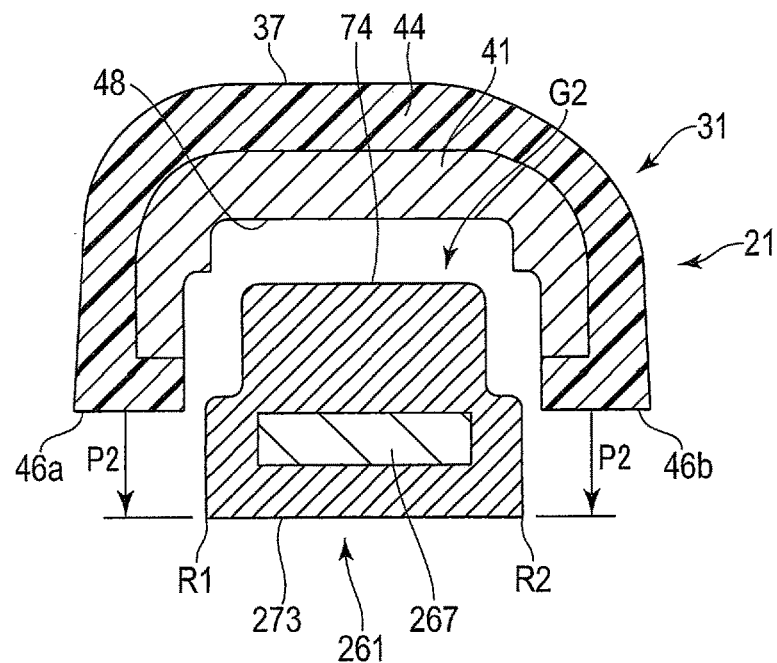
F I G. 14D
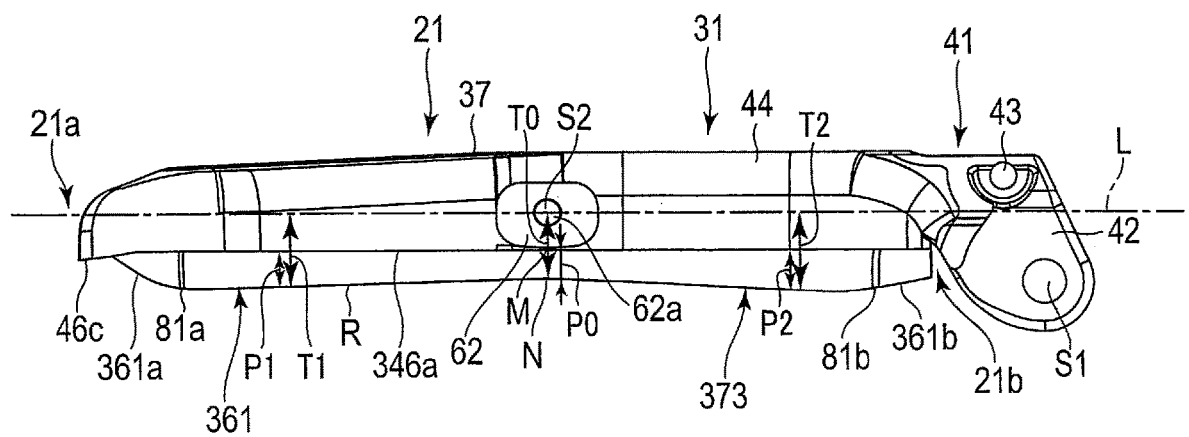
F I G. 15

GRASPING TREATMENT INSTRUMENT

CROSS-REFERENCE TO RELATED APPLICATIONS

This application is a Continuation Application of PCT Application No. PCT/JP2016/070720, filed Jul. 13, 2016, the entire contents of which are incorporated herein by reference.

BACKGROUND OF THE INVENTION

1. Field of the Invention

The present invention relates to a grasping treatment instrument which is configured to grasp biological tissues.

2. Description of the Related Art

For example, Jpn. Pat. Appln. KOKAI Publication No. 2008-264565 discloses first and second grasping pieces which can grasp biological tissues in cooperation. The first grasping piece includes a jaw which is turnable around a first rotary axis perpendicular to a longitudinal axis of a shaft, and a grasping member which is supported by the jaw. The grasping member is supported swingably around a second rotary axis substantially parallel to the first rotary axis with respect to the jaw. The grasping member appropriately swings to closely adhere a biological tissue between the grasping member and the second grasping piece in cooperation with the facing second grasping piece.

BRIEF SUMMARY OF THE INVENTION

According to one aspect of the present invention, a grasping treatment instrument includes a jaw and a grasping member. The jaw includes first rim and second rim juxtaposed to a longitudinal axis defined by a distal portion and a proximal portion of the jaw, and a recess with a bottom surface formed between the first rim and the second rim. The jaw is configured to be turnable around a first rotary axis intersecting with the longitudinal axis at the proximal portion. The grasping member includes a distal end region, proximal end region, and a ridge formed between the distal end region and the proximal end region of the grasping member. The ridge includes a distal end and a proximal end. The distal end is positioned at a proximal side with respect to the distal end region of the grasping member. The proximal end is positioned at a distal side with respect to the proximal end region of the grasping member. The grasping member is supported by the recess of the jaw turnably around a second rotary axis at a position between the distal end and the proximal end of the ridge on a distal side of the first rotary axis. The grasping member is configured to be turnable between a first position and a second position. At the first position, the grasping member is in contact with the bottom surface of the recess at a position on a distal side of the second rotary axis. At a second position, the grasping member is in contact with the bottom surface of the recess at a position on a proximal side of the second rotary axis. When the grasping member is positioned at the first position, a component of the ridge between the second rotary axis and the distal end of the ridge protrudes to the opposite side from the bottom surface of the recess with respect to the first rim and the second rim. When the grasping member is positioned at the second position, a component of the ridge between the second rotary axis and the proximal end of the ridge protrudes to the opposite side from the bottom surface of the recess with respect to the first rim and the second rim.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 2 is a schematic side view illustrating an end effector of the grasping treatment instrument according to the first embodiment.

FIG. 11A is a schematic view illustrating a neutral state where the grasping member is disposed swingably along a longitudinal axis of a jaw of a grasping piece of the grasping treatment instrument according to the second embodiment.

FIG. 11B is a cross-sectional view along an 11B-11B line of the grasping piece in FIG. 11A.

FIG. 14B is a cross-sectional view along a 14B-14B line of the grasping piece in FIG. 14A.

FIG. 14C is a cross-sectional view along a 14C-14C line of the grasping piece in FIG. 14A.

FIG. 14D is a cross-sectional view along a 14D-14D line of the grasping piece in FIG. 14A.

FIG. 15 is a schematic view illustrating a neutral state where a grasping member is disposed swingably along a longitudinal axis of a jaw of a grasping piece of a grasping treatment instrument according to a fourth embodiment.

DETAILED DESCRIPTION OF THE INVENTION

Modes for carrying out the present invention will be described with reference to the drawings below.

First Embodiment

Figure 1:
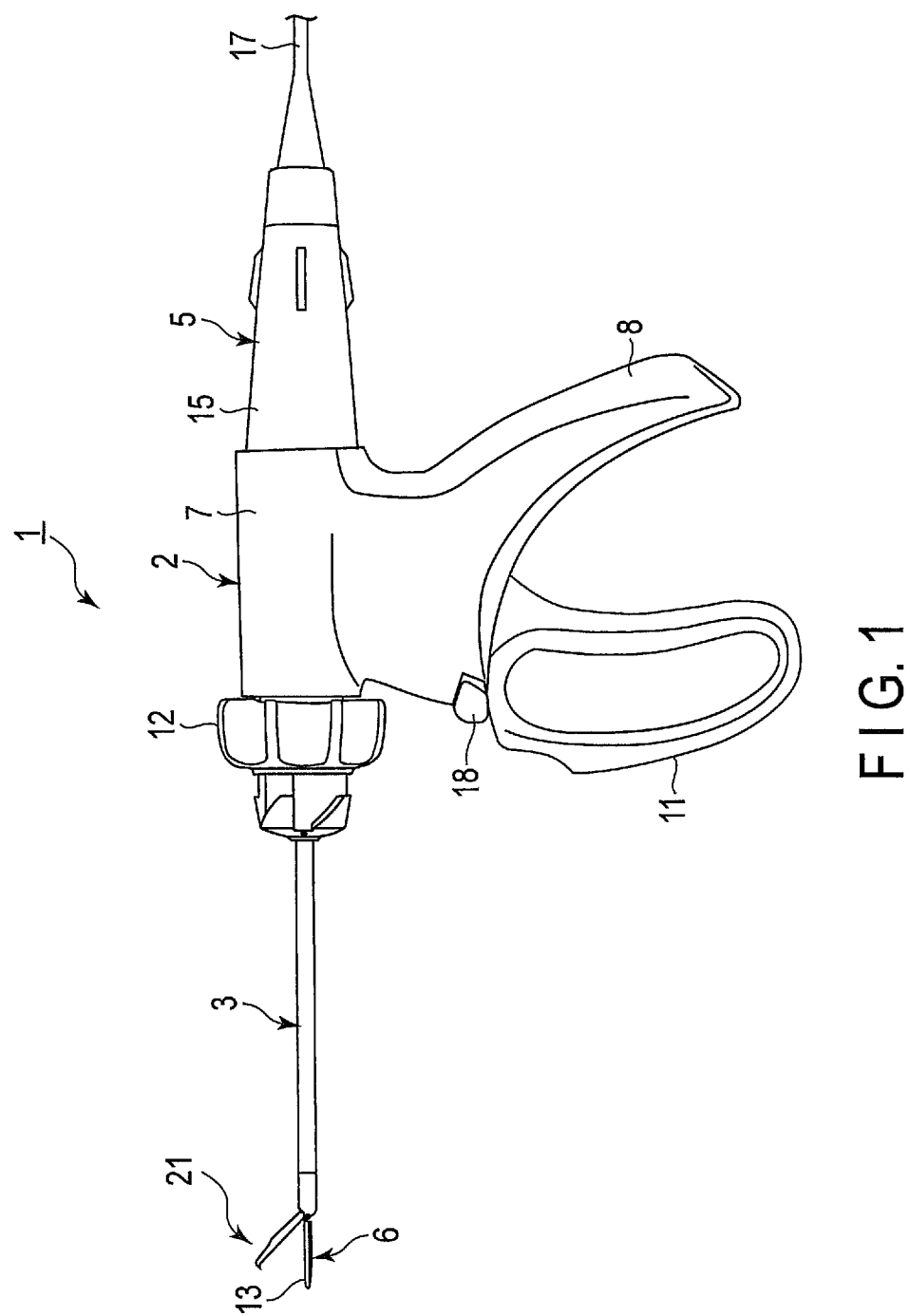
FIG. 1 is a schematic view illustrating a grasping treatment instrument according to first to third embodiments.
Figure 3:
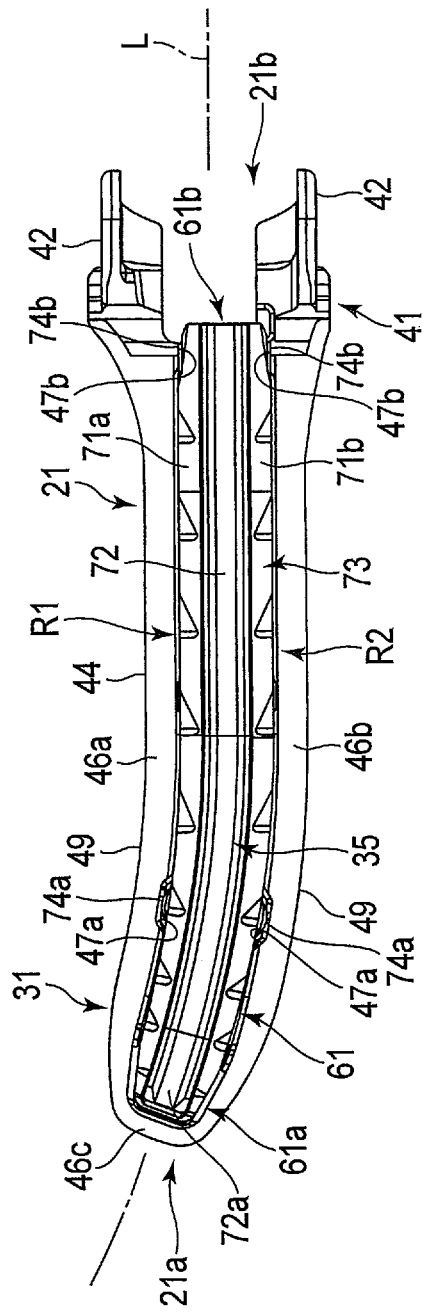
FIG. 3 is a schematic view illustrating a state where a grasping piece of the grasping treatment instrument according to the first embodiment is seen from a side of a treatment portion of a rod member.

The first embodiment of the present invention will be described with reference to FIGS. 1 to 8D. FIG. 1 is a view illustrating a grasping treatment instrument 1 according to the present embodiment. FIG. 2 illustrates a state where an end effector 10 is seen from one side in a width direction. FIG. 3 illustrates a state where a grasping piece 21 is seen from a side of a treatment surface (grasping region) 25 of a treatment portion 13 of a rod member 6.

As illustrated in FIG. 1, the grasping treatment instrument 1 includes a housing 2, a shaft 3, an ultrasonic transducer unit 5 and the rod member 6. The shaft 3 has a longitudinal axis C as a center axis. The shaft 3 extends along the longitudinal axis C.

The housing 2 can be held by an user, and is coupled to a proximal side of the shaft 3. The housing 2 includes a housing main body 7 which extends along the longitudinal axis C, and a grip 8 which extends from the housing main body 7 along a direction intersecting the longitudinal axis C. Furthermore, a handle 11 is turnably attached to the housing 2. When the handle 11 turns with respect to the housing 2 about an attachment position with respect to the housing 2, the handle 11 is opened or closed with respect to the grip 8. In addition, in the present embodiment, the handle 11 is located on a distal side of the grip 8, and a movement direction during an opening operation and a closing operation of the handle 11 with respect to the grip 8 is substantially parallel to the longitudinal axis C. However, the present embodiment is not limited to this. According to one embodiment, the handle 11 may be provided on the proximal side of the grip 8. Furthermore, according to another embodiment, the handle 11 and the grip 8 may be provided on opposite sides with the longitudinal axis C located at the center, and the movement direction during the opening operation and the closing operation of the handle 11 with respect to the grip 8 may be substantially vertical to the longitudinal axis C.

In the present embodiment, a rotation member (rotation knob) 12 is attached to the housing main body 7 from the distal side. The shaft 3 is inserted inside the rotation member 12 from the distal side. The shaft 3 is fixed to the rotation member 12, and can rotate about the longitudinal axis C together with the rotation member 12 with respect to the housing 2.

The rod member (probe) 6 can transmit ultrasonic vibration, and extends toward the distal side along the longitudinal axis C passing from the inside of the housing 2 to the inside of the shaft 3. As illustrated in FIG. 2, the rod member 6 includes the treatment portion (rod treatment portion) 13 at a distal portion of the rod member 6. The rod member 6 is inserted in the shaft 3 such that the treatment portion (rod side grasping piece) 13 protrudes from the distal end of the shaft 3 toward the distal side.

The transducer unit 5 illustrated in FIG. 1 includes a transducer case 15 and an unillustrated ultrasonic transducer. The transducer case 15 is attached to the housing main body 7 from the proximal side. The ultrasonic transducer is disposed inside the transducer case 15. The ultrasonic transducer extends along the longitudinal axis C, and the ultrasonic transducer is connected to the rod member 6 from the proximal side inside the housing main body 7. The ultrasonic transducer is detachably connected to an energy control device (not illustrated) via a cable 17, for example. The cable 17 may extend from the housing 2.

An operation button 18 is attached to the housing 2. The operation button 18 receives an input of an operation of outputting electrical energy from the energy control device. When the operation button 18 receives an input of an operation, the energy control device supplies, for example, alternating power of a predetermined frequency as the electrical energy to the ultrasonic transducer via an electric wiring (not illustrated) or the like inside the cable 17. Thus, the ultrasonic transducer in the transducer case 15 of the transducer unit 5 causes ultrasonic vibration. The ultrasonic vibration caused by the ultrasonic transducer transmits from the proximal side to the distal side in the rod member 6. Furthermore, the ultrasonic vibration is transmitted to the treatment portion 13 of the rod member 6. When the ultrasonic vibration is transmitted, the ultrasonic transducer and the rod member 6 vibrate at a frequency within a predetermined frequency range. In this case, a vibration direction of the rod member 6 and the ultrasonic transducer is substantially parallel to the longitudinal axis C. In addition, instead of the operation button 18 or in addition to the operation button 18, a foot switch which is separate from the grasping treatment instrument 1 may be provided.

As illustrated in FIG. 2, the grasping piece (jaw side grasping piece) 21 is disposed at the distal portion of the shaft 3. The grasping piece 21 includes a jaw (support member) 31 and a grasping member 61.

The jaw 31 is turnably attached around a first rotary axis S1 perpendicular to the longitudinal axis C. The first rotary axis S1 is perpendicular to a longitudinal axis L of the jaw 31 described below, too. A movable member 3a extends along the longitudinal axis C coaxially with the shaft 3. The movable member 3a may be provided on an inner side or an outer side of the shaft 3. A distal portion of the movable member 3a is coupled to a proximal portion of the jaw 31. The movable member 3a extends to the inside of the housing 2 illustrated in FIG. 1 toward the proximal side. The handle 11 is coupled to the movable member 3a inside the housing main body 7. When the handle 11 is opened or closed with respect to the grip 8, the movable member 3a moves along the longitudinal axis C. When the movable member 3a moves, a driving force acts on the jaw 31 via the movable member 3a, and the jaw 31 turns about the first rotary axis S1 of the distal portion of the shaft 3. Thus, the grasping piece 21 is opened or closed with respect to the treatment portion 13. When the grasping piece 21 and the treatment portion 13 are closed, it is possible to grasp a treatment target such as a biological tissue between the grasping piece 21 and the treatment portion 13. In addition, an opening direction and a closing direction of the grasping piece 21 intersects the longitudinal axis C. Furthermore, in a state where the grasping piece 21 and the treatment portion 13 are closed, a longitudinal direction (longitudinal axis L) of the grasping piece 21 is substantially parallel to the longitudinal axis C of the shaft 3.

In the present embodiment, the treatment portion 13 and the grasping piece 21 form the end effector 10. The end effector 10 can open and close the grasping piece 21 with respect to the treatment portion 13 of the rod member 6. Furthermore, the end effector 10, i.e., the grasping piece 21 and the treatment portion 13 of the rod member 6 can rotate around the longitudinal axis C together with the rotation member 12 and the shaft 3 with respect to the housing 2.

In addition, one embodiment may employ a configuration where the rotation member 12 is not provided, the shaft 3 and the end effector 10 (the grasping piece 21 and the treatment portion 13 of the rod member 6) do not rotate around the longitudinal axis C with respect to the housing 2.

Hereinafter, a direction which intersects (substantially vertical to) the longitudinal axis C illustrated in FIG. 2 and intersects (substantially vertical to) the opening direction and the closing direction of the grasping piece 21 is the width direction of the end effector 10. The treatment portion 13 of the rod member 6 includes the treatment surface (treatment portion facing surface) 25 which faces the grasping piece 21, and a back surface (treatment portion back surface) 27 which faces a side opposite to the treatment surface 25. The treatment surface 25 is used as a grasping region which is configured to grasp the biological tissue between the grasping region and a grasping surface 73 described below. More specifically, the treatment surface 25 faces a pad member 67 and is configured to grasp the biological tissue between the treatment surface 25 and the pad member 67. The treatment surface 25 includes at a distal portion a treatment portion inclined surface 28 which inclines with respect to the longitudinal axis C. The treatment portion inclined surface (rod side inclined surface) 28 inclines to a side of the back surface 27 of the treatment portion 13 toward the distal side. In the present embodiment, the treatment portion inclined surface 28 forms the distal end of the treatment surface 25 of the treatment portion 13, and extends from the distal end to the proximal side of the treatment surface 25. Furthermore, in the present embodiment, the treatment portion 13 includes at the distal portion a curved extension portion (rod curved portion) 29 which extends in a curved state with respect to the longitudinal axis C in the width direction of the end effector 10. In addition, it is preferable that the treatment portion inclined surface 28 is formed on the distal side of the curved extension portion (rod curved portion) 29 in the treatment portion 13.

Figure 4:
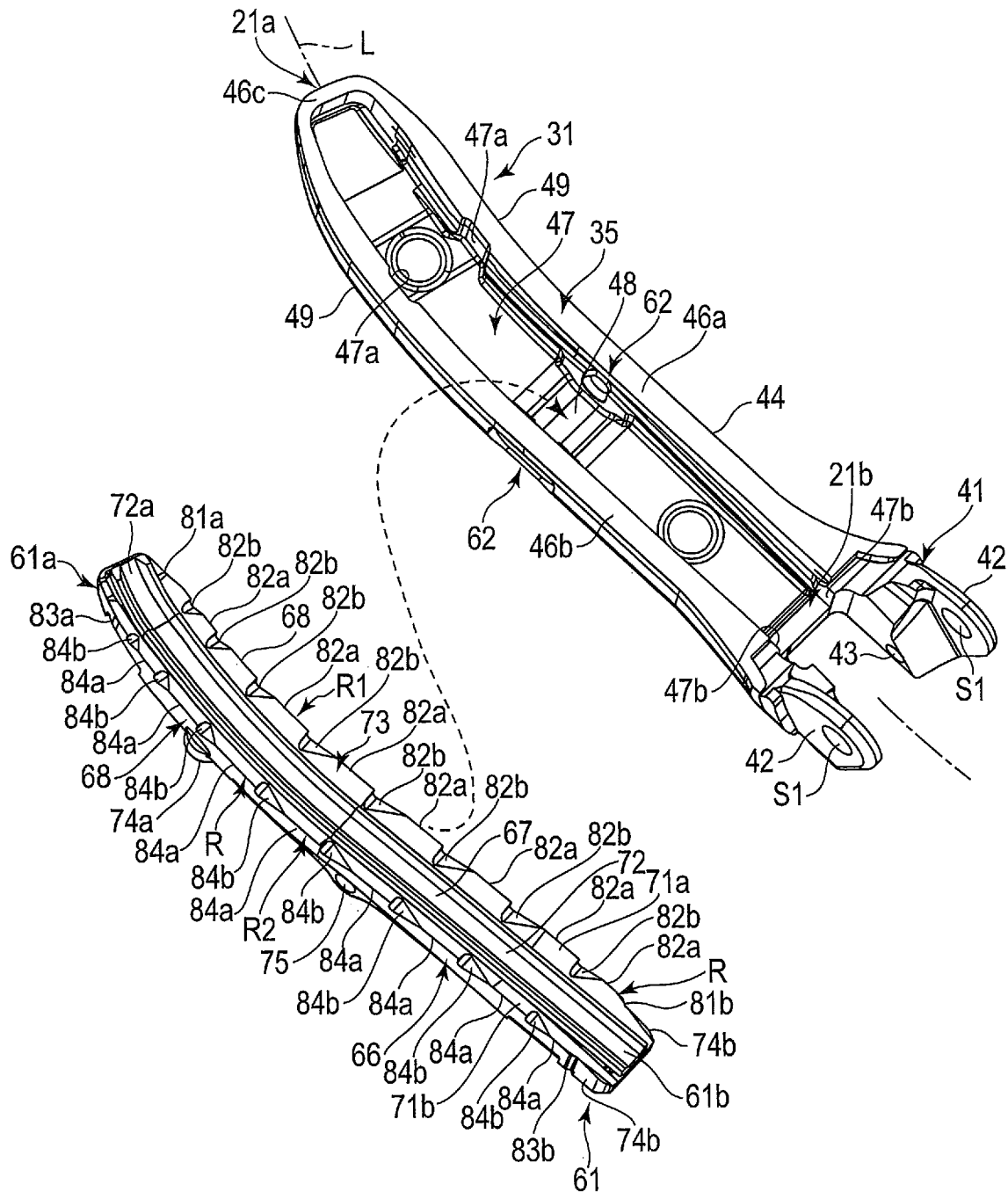
FIG. 4 is a schematic perspective view illustrating a state where the grasping piece of the grasping treatment instrument according to the first embodiment is separated to a jaw and a grasping member.
Figure 5A:
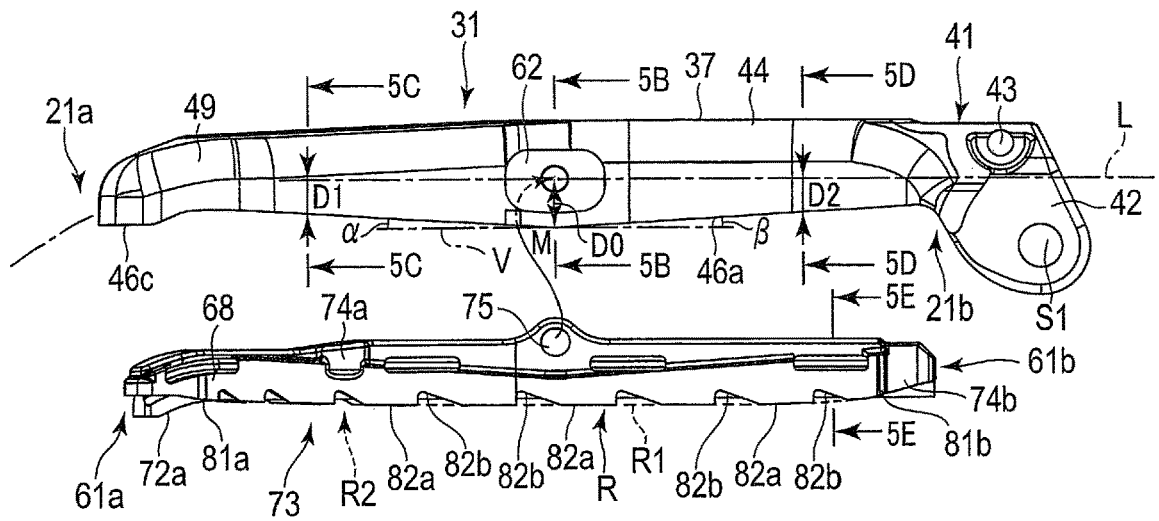
FIG. 5A is a schematic side view illustrating a state where the grasping piece of the grasping treatment instrument according to the first embodiment is separated to the jaw and the grasping member.
Figure 5B:
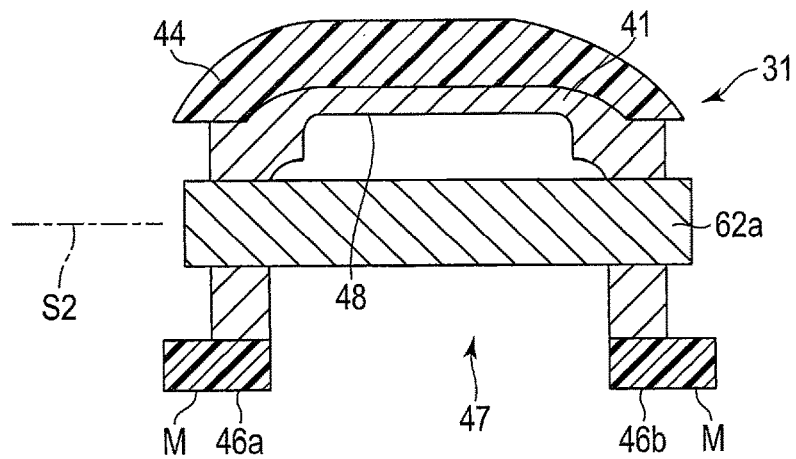
FIG. 5B is a cross-sectional view along a 5B-5B line of the jaw in FIG. 5A.
Figure 5C:
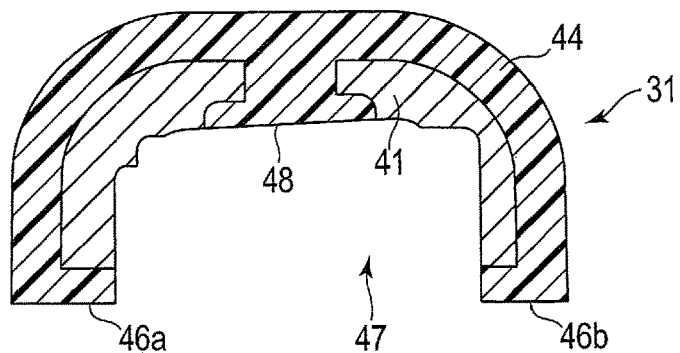
FIG. 5C is a cross-sectional view along a 5C-5C line of the jaw in FIG. 5A.
Figure 5D:
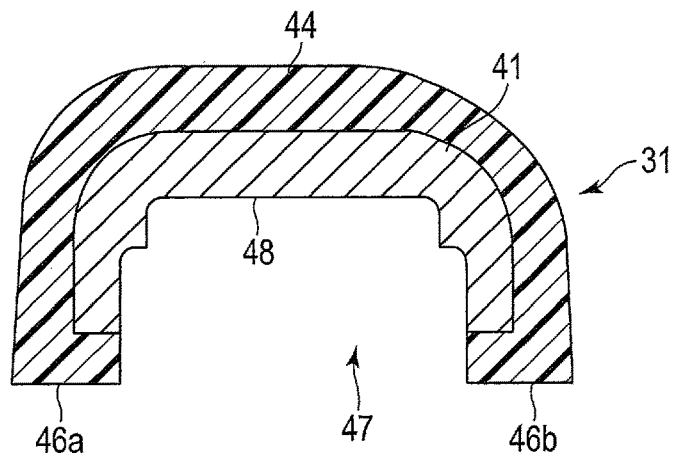
FIG. 5D is a cross-sectional view along a 5D-5D line of the jaw in FIG. 5A.

FIG. 4 is a perspective view illustrating a state where the jaw 31 of the grasping piece 21 and the grasping member 61 are separated. FIG. 5A is a side view illustrating a state where the jaw 31 of the grasping piece 21 and the grasping member 61 are separated. FIGS. 5B to 5D are cross-sectional views of a position illustrated in FIG. 5A.

As illustrated in FIG. 3, the grasping piece 21 defines the longitudinal axis L which is different from the longitudinal axis C between a distal portion 21a and a proximal portion 21b. The longitudinal axis L is perpendicular to a second rotary axis S2 described below. As illustrated in FIGS. 3 to 5D, the grasping piece 21 includes a facing surface 35 which faces the treatment portion 13 of the rod member 6, and a back surface (grasping piece back surface) 37 which faces a side opposite to the facing surface 35. The facing surface 35 of the grasping piece 21 faces toward a side on which the grasping piece 21 is closed, and the back surface 37 faces toward a side on which the grasping piece 21 is opened. In addition, the back surface 37 includes a side surface of the grasping piece 21.

The jaw 31 includes a jaw main body (support member) 41 formed by a metal, for example. The jaw main body 41 extends from the proximal portion 21b to the distal portion 21a of the grasping piece 21. The jaw main body 41 includes a turn support portion 42 at the proximal portion 21b. The turn support portion 42 is attached to the shaft 3 turnably around the first rotary axis S1 by a turning pin 42a illustrated in FIG. 2. Furthermore, the turn support portion 42 is coupled to a distal portion of the movable member 3a by a coupling portion 43 at a position different from the first rotary axis S1.

In the present embodiment, the jaw main body 41 is integrally insert-molded with, for example, a cover 44 made of a resin material having an electrical insulation property. Hence, the jaw 31 includes the cover 44 which has the electrical insulation property on at least part of an outer circumferential surface on a side opposite to a bottom surface 48 of a recess 47 described below. The cover 44 closely adheres to most of an outer surface of the jaw main body 41. Hence, most of the outer surface of the jaw main body 41 on the back surface 37 of the grasping piece 21 is not exposed to an outside of the grasping piece 21, and most of the back surface 37 of the grasping piece 21 is formed by the cover 44. In addition, one embodiment may employ a configuration where the cover 44 is a member different from the jaw main body 41 and the cover 44 is attached to the outer surface of the jaw main body 41. Furthermore, according to still another embodiment, instead of closely adhering the cover 44 to the outer surface of the jaw main body 41, a resin coating may be applied to the outer surface of the jaw main body 41. In addition, the cover 44 may be formed by a ceramic material or a rubber material, or a ceramic coating may be applied to the outer surface of the jaw main body 41.

As illustrated in FIGS. 4, and 5B to 5D, the jaw 31 is formed in a substantially half-pipe shape extending in a direction along the longitudinal axis L. Hence, the jaw 31 includes a first rim 46a and a second rim 46b juxtaposed to the longitudinal axis L, and the recess 47 formed between the first rim 46a and the second rim 46b. In addition, distal side portions of the first rim 46a and the second rim 46b are connected via a connection portion 46c which connects the first rim 46a and the second rim 46b. The connection portion 46c protects a distal side of a distal end region 61a between a distal end 81a of a first ridge R1 and a distal end 83a of a second ridge R2 of the grasping member 61 described below. The first rim 46a, the second rim 46b and the connection portion 46c are formed as part of the facing surface 35 of the grasping piece 21. The first rim 46a, the second rim 46b and the connection portion 46c are formed as part of the cover 44.

The recess 47 is recessed toward the side on which the grasping piece 21 is opened, and includes the bottom surface 48. The bottom surface 48 of the recess 47 extends from the proximal portion 21b to the distal portion 21a along the longitudinal axis L similar to the first rim 46a and the second rim 46b. The bottom surface 48 of the recess 47 is a surface on a side opposite to the back surface 37 of the jaw 31. Hereinafter, an example where the bottom surface 48 of the recess 47 is formed as part of the jaw main body 41 will be described. However, the bottom surface 48 may be formed as part of the cover 44. A center position of the jaw 31 in the width direction of the end effector 10 is continuously located in the recess 47 from a distal end of the recess 47 to a proximal end of the recess 47. The jaw 31 includes a curved extension portion 49 near the distal portion 21a including the connection portion 46c. The curved extension portion 49 is curved in the width direction facing the curved extension portion 29 of the treatment portion 13 of the rod member 6. The distal portion of the recess 47 of the jaw 31 also extends in a curved state with respect to the longitudinal axis L of the jaw 31 in the width direction of the end effector 10. Hence, the longitudinal axis L of the grasping piece 21 extends in a curved state in the width direction of the end effector 10 at the distal portion 21a of the jaw 31.

The jaw 31 includes turn support portions 62 to which the grasping member 61 is attached via a support pin 62a (second rotary axis S2) illustrated in FIGS. 2 and 3. The support pin 62a (second rotary axis S2) is parallel or substantially parallel to the first rotary axis S1 in the present embodiment. The support pin 62a (second rotary axis S2) may be disposed in the curved extension portion 49, for example. In this case, the support pin 62a (second rotary axis S2) may be parallel or substantially parallel to the first rotary axis S1 or may be at a skew position.

The grasping member 61 includes a grasping member main body 66 and the pad member 67.

The grasping member main body 66 is formed by a metal having conductivity, and extends from the proximal portion 21b to the distal portion 21a of the grasping piece 21. Furthermore, the grasping member main body 66 includes a curved extension portion 68 at a distal portion similar to the curved extension portion 49 of the jaw 31. Hence, the distal portion of the grasping member main body 66 extends in a curved state in the width direction of the end effector 10.

The grasping member 61 is supported by the jaw 31 in a state where the grasping member 61 is inserted in the recess 47 of the jaw 31. The grasping member 61 includes a turn support portion 75 on a side of a back surface 74 with respect to one pair of inclined surfaces 71a and 71b. The turn support portion 75 of the grasping member 61 is supported turnably around the second rotary axis S2 parallel or substantially parallel to the first rotary axis S1 at a position on the distal side of the first rotary axis S1 along the longitudinal axis L by the recess 47 of the jaw 31. More specifically, the turn support portion 75 of the grasping member 61 is supported via the turn pin 62a with respect to the turn support portion 62 of the jaw 31. Consequently, the grasping member 61 is swingable with respect to the jaw 31. In addition, although as described above, it is preferable that the second rotary axis S2 is at a skew position with respect to the first rotary axis S1.

Figure 5E:
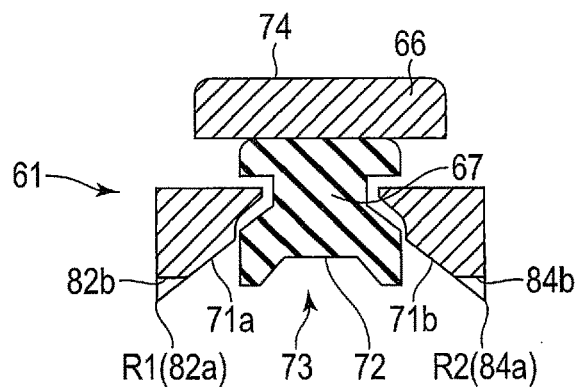
FIG. 5E is a cross-sectional view along a 5E-5E line of the grasping member in FIG. 5A.

As illustrated in FIGS. 4 and 5E, the grasping member main body 66 includes one pair of inclined surfaces 71a and 71b as biological tissue grasping surfaces. The pad member 67 is attached between one pair of inclined surfaces 71a and 71b. That is, the pad member 67 is attached to the grasping member main body 66. It is preferable that the pad member 67 is formed by a resin material such as PTFE (polytetrafluoroethylene) or the like, and has elasticity. The pad member 67 is formed from a material which suppresses abrasion due to friction with the treatment portion 13 of the rod member 6 as much as possible, and has a thermal resistance. Furthermore, it is preferable that the pad member 67 has an electrical insulation property. Hence, it is also preferable that the pad member 67 is formed by a rubber material, a ceramic material or the like. The pad member 67 includes a facing surface 72 which faces the treatment surface 25 of the treatment portion 13 illustrated in FIG. 2 between one pair of inclined surfaces 71a and 71b. Furthermore, the facing surface 72 of the pad member 67 forms the grasping surface 73 of the grasping piece 21 in cooperation with one pair of inclined surfaces 71a and 71b of the grasping member main body 66.

A pad inclined surface 72a which inclines with respect to the longitudinal direction of the grasping piece 21 is formed at a distal portion of the facing surface 72 of the pad member 67 of the grasping member 61. The pad inclined surface 72a inclines to a side on which the grasping piece 21 is closed toward the distal side. That is, the pad inclined surface 72a inclines to the side of the treatment portion 13 toward the distal side. The pad inclined surface 72a faces the treatment portion inclined surface 28 of the treatment portion 13 of the rod member 6. Furthermore, in a state where the facing surface 72 of the pad member 67 is in contact with the treatment surface 25 of the treatment portion 13, the pad inclined surface 72a is in contact with the treatment portion inclined surface 28. In a state where the pad member 67 is in contact with the treatment portion 13, it is preferable that the pad inclined surface 72a is substantially parallel to the treatment portion inclined surface 28. Furthermore, the pad inclined surface 72a protrudes toward the treatment portion 13 compared to a portion other than the pad inclined surface 72a of the facing surface 72.

As illustrated in FIGS. 4, 5A and 5E, the grasping member main body 66 includes a ridge R (R1 and R2) which is configured to grasp the biological tissue. The ridge R includes the first ridge (first tooth tip ridgeline) R1 which is close to the first rim 46a and is juxtaposed to the first rim 46a, and the second ridge (second tooth tip ridgeline) R2 which is close to the second rim 46b and is juxtaposed to the second rim 46b. The first ridge R1 and the second ridge R2 are each formed as a tooth which is configured to bite the biological tissue, and prevents slippery against the biological tissue. The first ridge R1 is adjacent to the inner side in the width direction of the first rim 46a of the jaw 31. The second ridge R2 is adjacent to the inner side in the width direction of the second rim 46b of the jaw 31.

In this regard, a region on a distal side of the distal end 81a of the first ridge R1 and the distal end 83a of the second ridge R2 is used to pinch (grasp) the biological tissue at the distal portion of the end effector 10 formed by the pad inclined surface 72a of the pad member 67 and the treatment portion inclined surface 28 of the treatment portion 13 of the rod member 6. Hence, it is preferable that the distal end 81a of the first ridge R1 and the distal end 83a of the second ridge R2 are on the proximal side of the distal end region (distal end portion) 61a at the distalmost end of the grasping member 61. A region on the proximal side of a proximal end 81b of the first ridge R1 and a proximal end 83b of the second ridge R2 is less likely to be used to grasp the biological tissue. Hence, it is preferable that the proximal end 81b of the first ridge R1 and the proximal end 83b of the second ridge R2 are on the distal side of a proximal end region (proximal end portion) 61b at the proximalmost end of the grasping member 61. Hence, the teeth (first ridge R1 and the second ridge R2) which are configured to bite the biological tissue are formed in most regions from the distal end to the proximal end of the grasping member 61, yet do not need to be formed in the entire region.

The first ridge R1 includes a plurality of first tooth tip regions 82a, and first recessed regions 82b which are formed between the first tooth tip regions 82a and recessed toward the back surface 74 of the grasping member 61 compared to the first tooth tip regions 82a in a region between the distal end 81a and the proximal end 81b. The second ridge R2 includes a plurality of second tooth tip regions 84a, and second recessed regions 84b which are formed between the second tooth tip regions 84a and are recessed toward the back surface 74 of the grasping member 61 compared to the second tooth tip regions 84a in a region between the distal end 83a and the proximal end 83b. The first recessed regions 82b and the second recessed regions 84b play a role of fishhook barbs. Consequently, the first recessed regions 82b and the second recessed regions 84b are formed, so that it is possible to firmly grasp the biological tissue.

In addition, the grasping member 61 is swingable in a turning range between the neutral position (see FIG. 6A) along the longitudinal axis L of the jaw 31, and the first position (see FIG. 7A) and the second position (see FIG. 8A) shifted from the longitudinal axis L of the jaw 31.

As illustrated in FIGS. 6A to 6D, at the neutral position (an intermediate position between the first position and the second position) at which the grasping member 61 extends substantially parallel to the longitudinal axis L of the jaw 31, the back surface 74 of the grasping member 61 is apart with a gap from the bottom surface 48 of the recess 47 and is not in contact with the bottom surface 48.

Figure 6B:
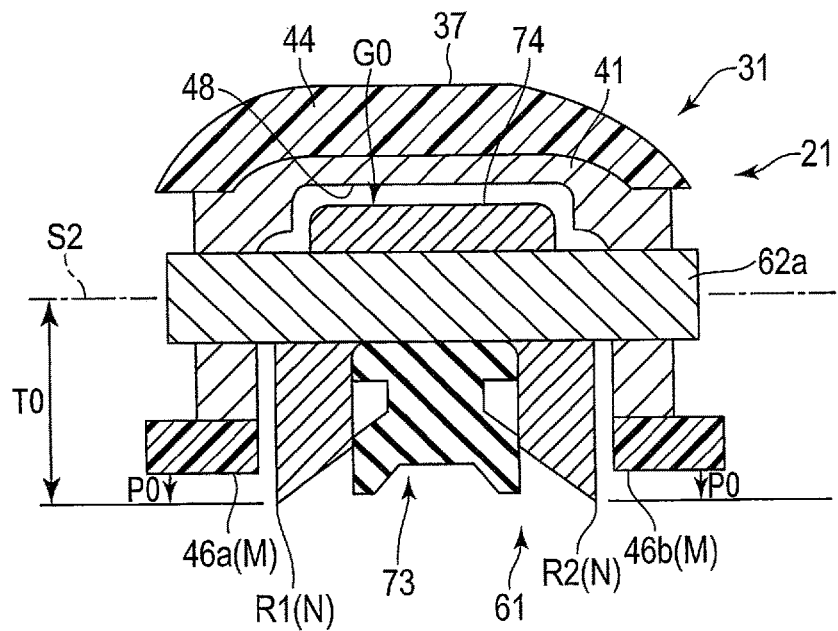
FIG. 6B is a cross-sectional view along a 6B-6B line of the grasping piece in FIG. 6A.
Figure 6C:
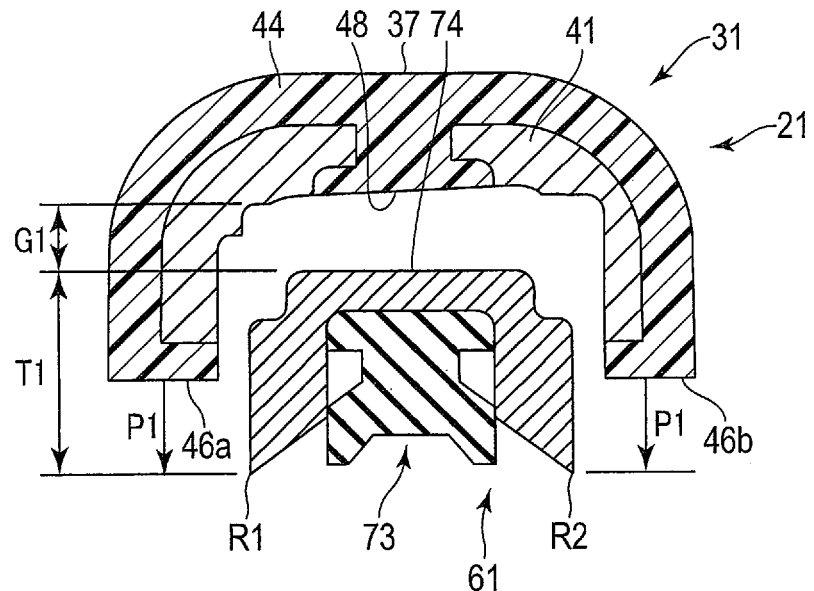
FIG. 6C is a cross-sectional view along a 6C-6C line of the grasping piece in FIG. 6A.
Figure 6D:
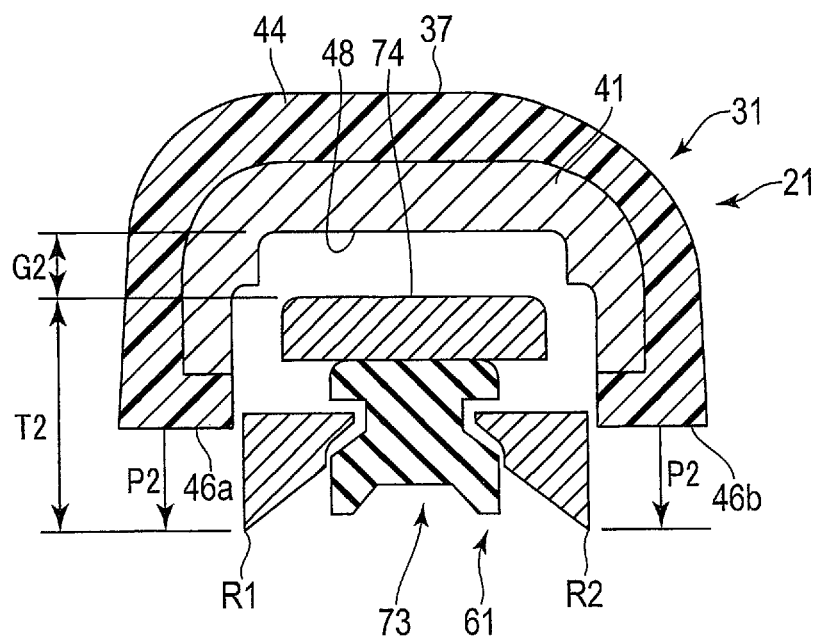
FIG. 6D is a cross-sectional view along a 6D-6D line of the grasping piece in FIG. 6A.
Figure 7A:
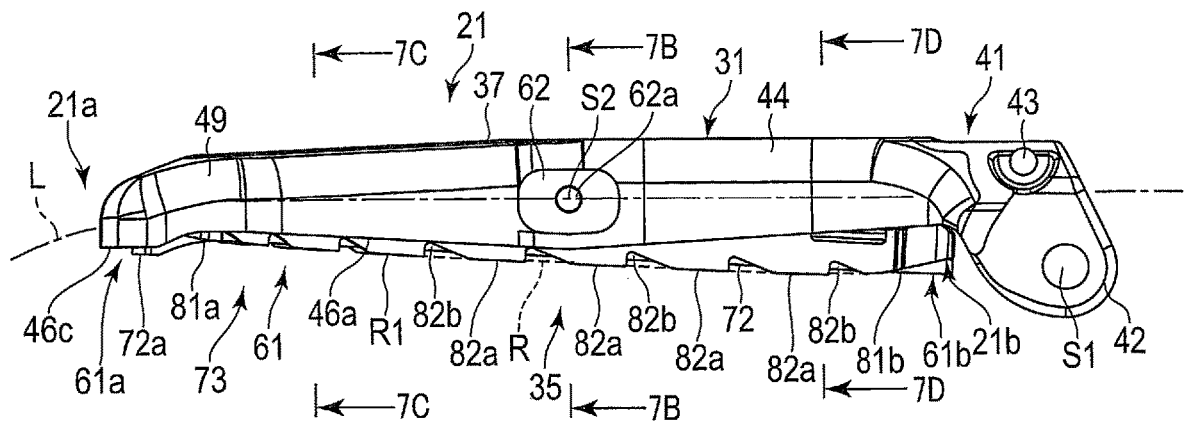
FIG. 7A is a schematic view illustrating a first position at which a back surface of the grasping member is placed in contact with a position on a distal side of a second rotary axis on a bottom surface of a recess of the jaw of the grasping piece of the grasping treatment instrument according to the first embodiment.
Figure 7B:
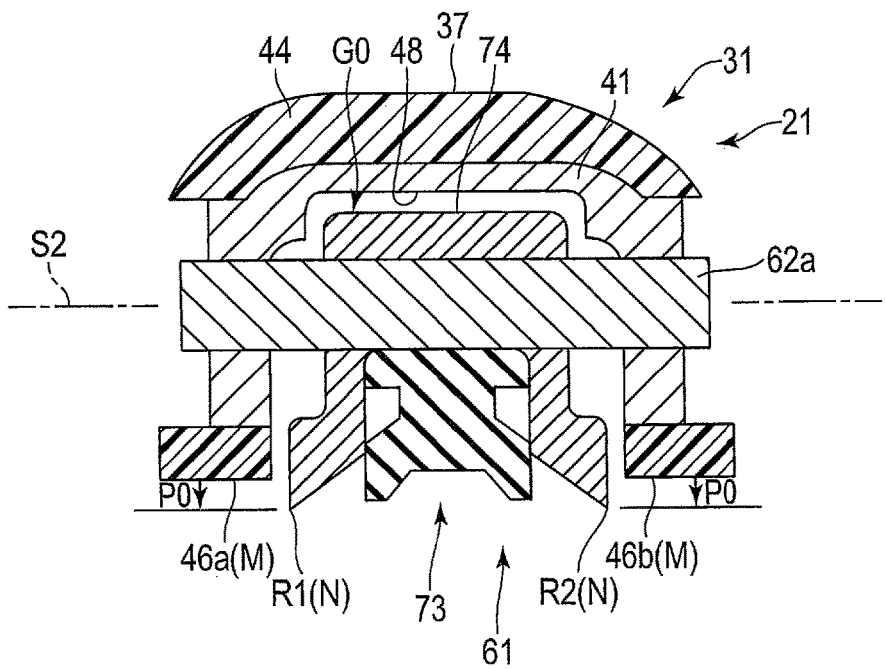
FIG. 7B is a cross-sectional view along a 7B-7B line of the grasping piece in FIG. 7A.
Figure 7C:
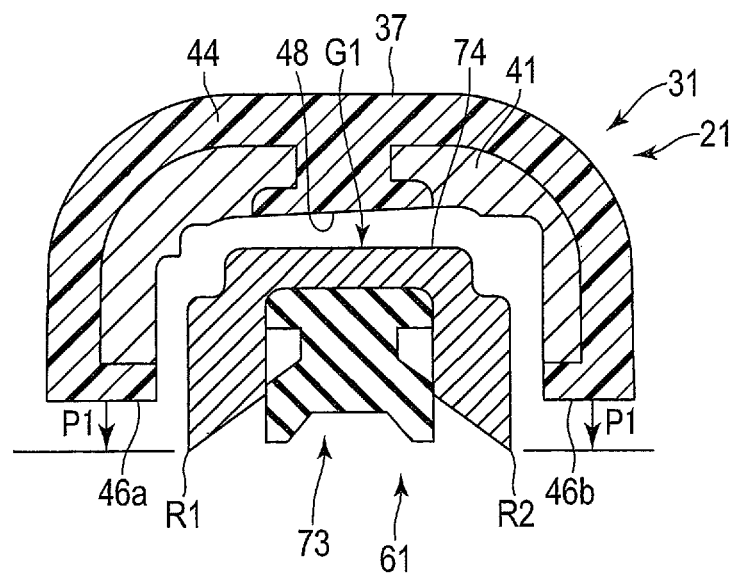
FIG. 7C is a cross-sectional view along a 7C-7C line of the grasping piece in FIG. 7A.
Figure 7D:
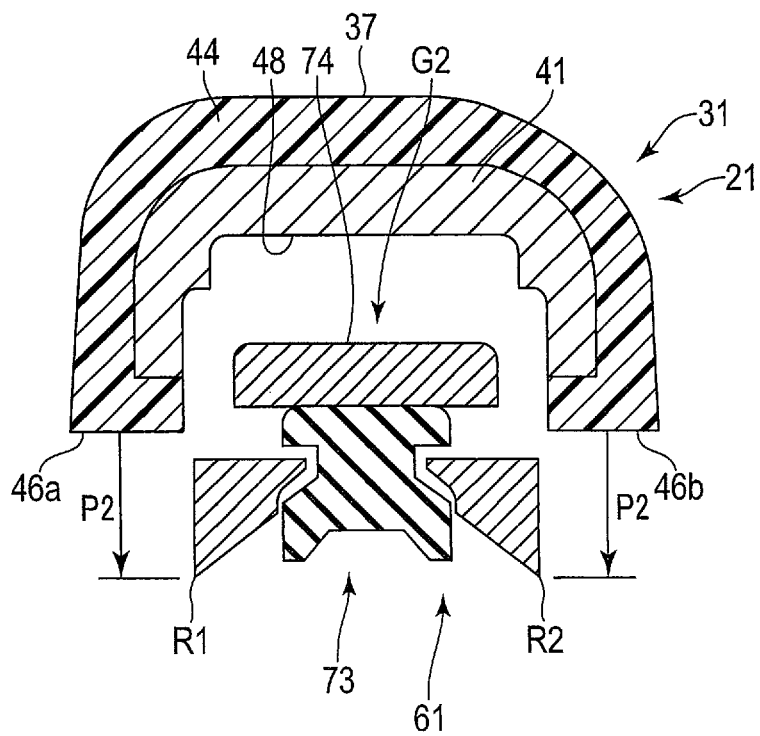
FIG. 7D is a cross-sectional view along a 7D-7D line of the grasping piece in FIG. 7A.

At the first position illustrated in FIG. 7A, the position of the back surface 74 of the grasping member 61 on the distal side of the second rotary axis S2 is in contact with the bottom surface 48 of the recess 47. Thus, the back surface 74 of the grasping member 61 is in contact with the bottom surface 48 of the recess 47 of the jaw 31, and thereby the grasping member 61 is restricted from swinging to one side. It is preferable that a vicinity of a distal end of the back surface 74 of the grasping member 61 is in contact with the bottom surface 48 of the recess 47 of the grasping piece 21. In this case, as illustrated in FIGS. 6B and 7B, at the substantially same position as the second rotary axis S2 in a direction along the longitudinal axis L, a gap G0 between the back surface 74 of the grasping member 61 and the bottom surface 48 of the recess 47 of the jaw 31 does not change and is substantially constant distance. At a position on the distal side of the second rotary axis S2, a gap G1 at the first position illustrated in FIG. 7C is smaller than the gap G1 at the neutral position illustrated in FIG. 6C. At a position on the proximal side of the second rotary axis S2, a gap G2 at the first position illustrated in FIG. 7D is larger than the gap G2 at the neutral position illustrated in FIG. 6D.

Figure 8A:
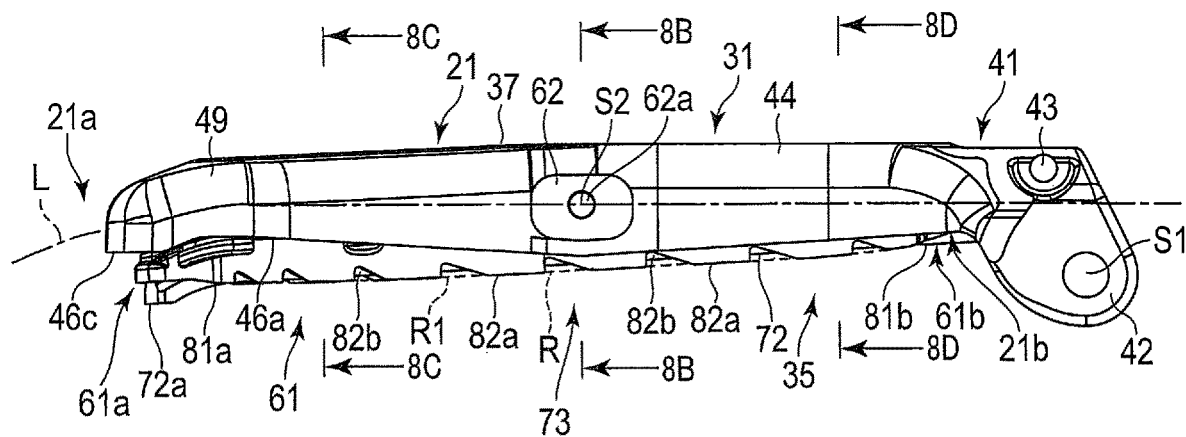
FIG. 8A is a schematic view illustrating a second position at which the back surface of the grasping member is placed in contact with a position on a proximal side of the second rotary axis on the bottom surface of the recess of the jaw of the grasping piece of the grasping treatment instrument according to the first embodiment.
Figure 8B:
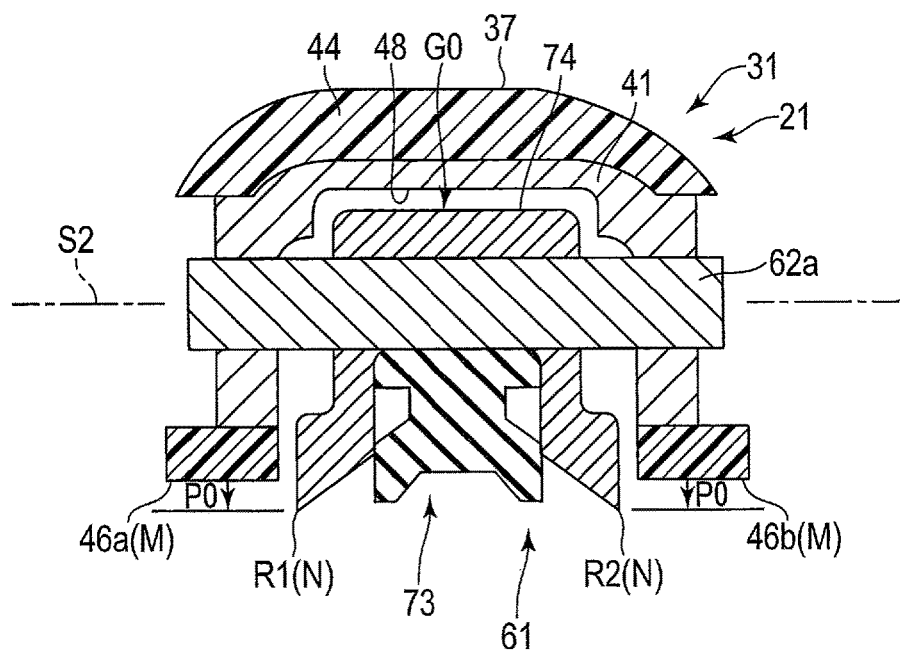
FIG. 8B is a cross-sectional view along an 8B-8B line of the grasping piece in FIG. 8A.
Figure 8C:
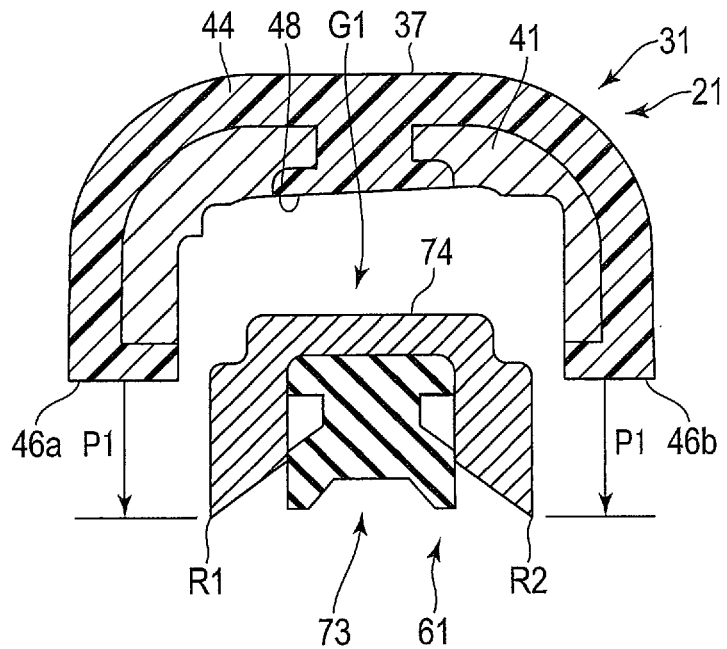
FIG. 8C is a cross-sectional view along an 8C-8C line of the grasping piece in FIG. 8A.
Figure 8D:
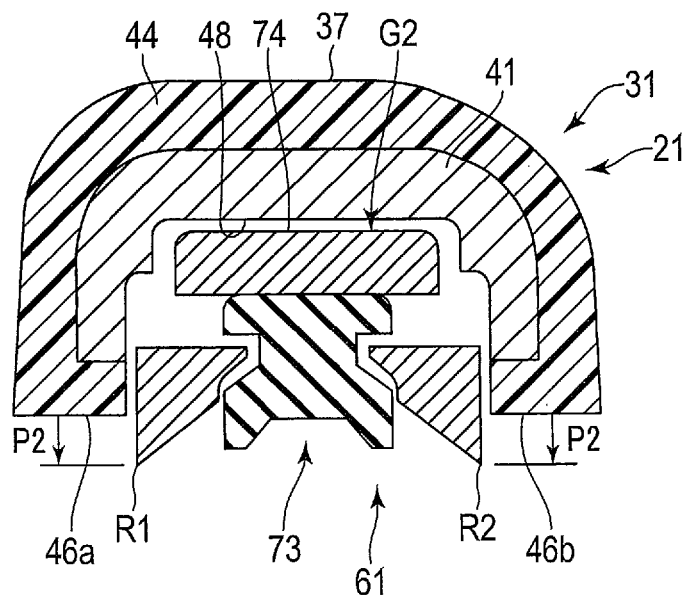
FIG. 8D is a cross-sectional view along an 8D-8D line of the grasping piece in FIG. 8A.

At the second position illustrated in FIG. 8A, the position of the back surface 74 of the grasping member 61 on the proximal side of the second rotary axis S2 is in contact with the bottom surface 48 of the recess 47. Thus, the back surface 74 of the grasping member 61 is in contact with the bottom surface 48 of the recess 47 of the jaw 31, and thereby is restricted from swinging to the other side. It is preferable that a vicinity of a proximal end of the back surface 74 of the grasping member 61 is in contact with the bottom surface 48 of the recess 47 of the grasping piece 21. In this case, as illustrated in FIGS. 6B and 8B, at the substantially same position as the second rotary axis S2 in a direction along the longitudinal axis L, the gap G0 between the back surface 74 of the grasping member 61 and the bottom surface 48 of the recess 47 of the jaw 31 does not change and is substantially constant distance. At the position on the distal side of the second rotary axis S2, the gap G1 at the second position illustrated in FIG. 8C is larger than the gap G1 at the neutral position illustrated in FIG. 6C. At the position on the proximal side of the second rotary axis S2, the gap G2 at the second position illustrated in FIG. 8D is smaller than the gap G2 at the neutral position illustrated in FIG. 6D.

Figure 6A:
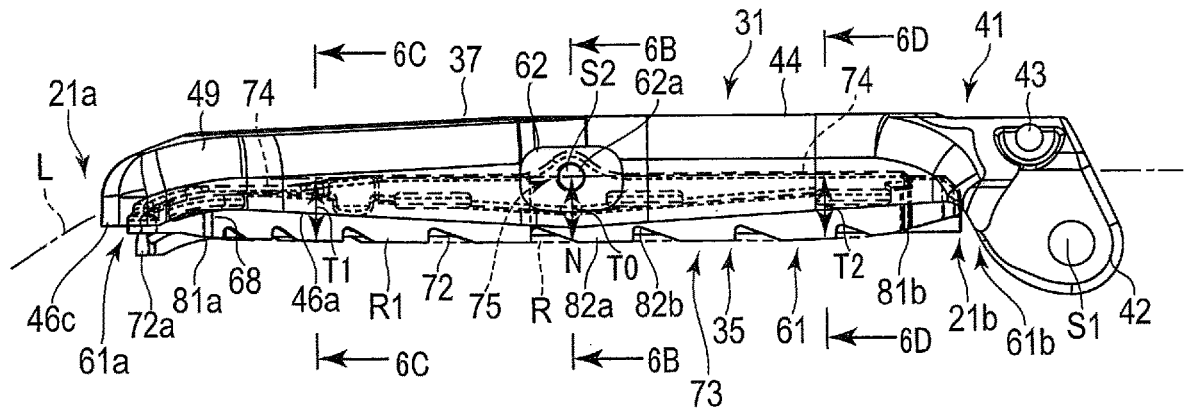
FIG. 6A is a schematic view illustrating a neutral state where the grasping member is disposed swingably along a longitudinal axis of the jaw of the grasping piece of the grasping treatment instrument according to the first embodiment.

In addition, when moving from the first position illustrated in FIG. 7A to the second position illustrated in FIG. 8A with respect to the jaw 31, the grasping member 61 passes the neutral position illustrated in FIG. 6A at all times. Similarly, when moving from the second position illustrated in FIG. 8A to the first position illustrated in FIG. 7A, the grasping member 61 passes the neutral position illustrated in FIG. 6A at all times.

Furthermore, in the present embodiment, as illustrated in FIGS. 5A to 5D, the first rim 46a is not formed in parallel yet inclines with respect to the longitudinal axis L. A maximum distance between the first rim 46a and the longitudinal axis L intersecting the second rotary axis S2 is formed at a position M near the second rotary axis S2. This distance is D0. At any position from the position M near the second rotary axis S2 to the distal portion 21a, a distance D1 between the first rim 46a and the longitudinal axis L is shorter than a distance D0. In this case, the distance D1 between the first rim 46a and the longitudinal axis L gradually becomes shorter from the position M near the second rotary axis S2 toward the distal portion 21a. An angle of the first rim 46a from the position M to the distal portion 21a with respect to a virtual line V parallel to the longitudinal axis L passing the position M near the second rotary axis S2 is formed as an angle α. The angle α is fixed in FIG. 5A, yet may change according to a position. At any position from the position M near the second rotary axis S2 to the proximal portion 21b, a distance D2 between the first rim 46a and the longitudinal axis L is shorter than the distance D0. In this case, the distance D2 between the first rim 46a and the longitudinal axis L gradually becomes shorter from the position M near the second rotary axis S2 toward the proximal portion 21b. In addition, an angle of the first rim 46a from the position M to the proximal portion 21b with respect to the virtual line V parallel to the longitudinal axis L passing the position M near the second rotary axis S2 is formed as an angle β. The angle β is fixed in FIG. 5A, yet may change according to a position. Hence, here the first rim 46a is formed in a substantially V shape between the position M near the second rotary axis S2 and the position from the position M to the distal portion 21a and the proximal portion 21b. In addition, the angles α and β may be the same or different.

In addition, similar to the first rim 46a, in a case of the second rim 46b, too, the distance D1 between the second rim 46b and the longitudinal axis L gradually becomes shorter from the position near the second rotary axis S2 toward the distal portion 21a. The distance D2 between the second rim 46b and the longitudinal axis L gradually becomes shorter from the position near the second rotary axis S2 toward the proximal portion 21b. Hence, here the second rim 46b is also formed in a substantially V shape similar to the first rim 46a.

Hence, the first rim 46a and the second rim 46b are apart from the ridges R1 and R2 of the grasping member 61 from the vicinity M of the second rotary axis S2 toward the distal portion 21a and the proximal portion 21b.

As illustrated in FIGS. 6A to 6D, it is preferable that the first ridge. R1 is parallel or substantially parallel to the longitudinal axis L at the neutral position. In this case, the first ridge R1 is not parallel to but slightly inclines with respect to the longitudinal axis L. A maximum distance (T0) between the first ridge R1 and the longitudinal axis L is formed at a position N near the second rotary axis S2. At any position from the position N near the second rotary axis S2 to the distal portion 21a, a distance T1 between the first ridge R1 and the longitudinal axis L is slightly shorter than a distance T0 (T1<T0). At any position from the position N near the second rotary axis S2 to the proximal portion 21b, a distance T2 between the first ridge R1 and the longitudinal axis L is slightly shorter than the distance T0 (T2<T0). Furthermore, the distance T1 between the first ridge R1 and the longitudinal axis L gradually becomes shorter from the position N near the second rotary axis S2 to the distal portion 21a. The distance T2 between the first ridge R1 and the longitudinal axis L gradually becomes shorter from the position N near the second rotary axis S2 to the proximal portion 21b. However, a distance (T1-D1) is longer than a distance (T0-D0). Furthermore, a distance (T2-D2) is longer than the distance (T0-D0). Hence, at the neutral position, the first rim 46a and the second rim 46b become gradually apart from the first ridge R1 of the grasping member 61 from the vicinity M of the second rotary axis S2 toward the distal portion 21a and the proximal portion 21b.

At the neutral position illustrated in FIG. 6C and at a position on a distal side of the second rotary axis S2, a gap G1 between the back surface 74 of the grasping member 61 and the bottom surface 48 of the recess 47 of the jaw 31 is smaller than a protrusion amount P1 between the first rim 46a and the first ridge R1 (G1<P1). Hence, when the grasping member 61 swings from the neutral position with respect to the jaw 31 as illustrated in FIG. 7A and is disposed at the first position, as illustrated in FIGS. 7B and 7D, the first ridge R1 naturally protrudes from the first rim 46a at the position on the proximal side of the second rotary axis S2 and at the substantially same position as the second rotary axis S2 in the direction along the longitudinal axis L. Furthermore, as illustrated in FIG. 7C, the first ridge R1 protrudes from the first rim 46a even at the position on the distal side of the second rotary axis S2. The same applies to a relationship between the second ridge R2 and the second rim 46b, too.

At the neutral position illustrated in FIG. 6D and at the position on the proximal side of the second rotary axis S2, a gap G2 between the back surface 74 of the grasping member 61 and the bottom surface 48 of the recess 47 of the jaw 31 is smaller than a protrusion amount P2 between the first rim 46a and the first ridge R1 (G2<P2). Hence, when the grasping member 61 swings from the neutral position with respect to the jaw 31 as illustrated in FIG. 5A and is disposed at the second position, as illustrated in FIGS. 8B and 8C, the first ridge R1 naturally protrudes from the first rim 46a at the position on the distal side of the second rotary axis S2 and at the substantially same position as the second rotary axis S2 in the direction along the longitudinal axis L. Furthermore, as illustrated in FIG. 8D, the first ridge R1 protrudes from the first rim 46a even at the position on the proximal side of the second rotary axis S2. The same applies to a relationship between the second ridge R2 and the second rim 46b, too.

Thus, a plurality of first tooth tip regions 82a of the first ridge R1 protrudes from the first rim 46a in a region between the distal end 81a and the proximal end 81b in all states illustrated in FIGS. 6A to 8D (P0>0, P1>G1>0 and P2>G2>0). Similarly, a plurality of second tooth tip regions 84a of the second ridge R2 protrudes from the second rim 46b in a region between the distal end 83a and the proximal end 83b in all states illustrated in FIGS. 6A to 8D (P0>0, P1>G1>0 and P2>G2>0). Consequently, when the grasping member 61 which is swingable with respect to the jaw 31 is used to grasp the biological tissue, a plurality of first tooth tip regions 82a of the first ridge R1 and a plurality of second tooth tip regions 84a of the second ridge R2 can be reliably placed in contact with the biological tissue.

It is preferable that the first recessed regions 82b between the first tooth tip regions 82a protrude from the first rim 46a in the region between the distal end 81a and the proximal end 81b in all states illustrated in FIGS. 6A to 8D. Similarly, it is preferable that the second recessed regions 84b between the second tooth tip regions 84a protrude from the second rim 46b in the region between the distal end 83a and the proximal end 83b in all states illustrated in FIGS. 6A to 8D. Consequently, when the biological tissue is grasped, a plurality of first tooth tip regions 82a of the first ridge R1 and a plurality of second tooth tip regions 84a of the second ridge R2 can not only be placed in contact with the biological tissue, but also bite the biological tissue in a state where the first recessed regions 82b and the second recessed region 84b which function as fishhook barbs prevent slippery.

Hence, when, for example, the biological tissue is grasped at the position N near the second rotary axis S2 along the longitudinal axis L, all of the first tooth tip regions 82a and the first recessed regions 82b of the first ridge R1 protrude from the first rim 46a toward the side opposite to the back surface 37 as illustrated in FIG. 6A. As illustrated in FIGS. 6B to 6D, all of the second tooth tip regions 84a and the second recessed regions 84b of the second ridge R2 protrude from the second rim 46b toward the side opposite to the back surface 37. Consequently, the first ridge R1 (the first tooth tip regions 82a and the first recessed regions 82b) and the second ridge R2 (the second tooth tip regions 84a and the second recessed regions 84b) can bite and grasp the biological tissue fast.

When, for example, the biological tissue is grasped at a position on the distal side of the position N near the second rotary axis S2 along the longitudinal axis L, all of the first tooth tip regions 82a and the first recessed regions 82b of the first ridge R1 protrude from the first rim 46a toward the side opposite to the back surface 37 as illustrated in FIG. 7A. As illustrated in FIGS. 7B to 7D, all of the second tooth tip regions 84a and the second recessed regions 84b of the second ridge R2 protrude from the second rim 46b toward the side opposite to the back surface 37. Consequently, the first ridge R1 (the first tooth tip regions 82a and the first recessed regions 82b) and the second ridge R2 (the second tooth tip regions 84a and the second recessed regions 84b) can bite and grasp the biological tissue fast.

When, for example, the biological tissue is grasped at a position on the proximal side of the position N near the second rotary axis S2 along the longitudinal axis L, all of the first tooth tip regions 82a and the first recessed regions 82b of the first ridge R1 protrude from the first rim 46a toward the side opposite to the back surface 37 as illustrated in FIG. 8A. As illustrated in FIGS. 8B to 8D, all of the second tooth tip regions 84a and the second recessed regions 84b of the second ridge R2 protrude from the second rim 46b toward the side opposite to the back surface 37. Consequently, the first ridge R1 (the first tooth tip regions 82a and the first recessed regions 82b) and the second ridge R2 (the second tooth tip regions 84a and the second recessed regions 84b) can bite and grasp the biological tissue fast.

Not only at the neutral position but also at the first position and the second position, and in the region between the distal portion 21a and the proximal portion 21b of the jaw 31, the ridges R1 and R2 protrude from the first rim 46a toward a side opposite to a direction traveling toward the bottom surface 48 of the recess 47, and protrude from the second rim 46b toward a side opposite to the direction traveling toward the bottom surface 48 of the recess 47. Consequently, when the biological tissue is grasped between the grasping surface 73 of the grasping piece 21 and the treatment surface 25 of the treatment portion 13 of the rod member 6, the ridges R1 and R2 of the grasping surface 73 can bite the biological tissue even in a case where the biological tissue is grasped at any position. In this state, the operation button 18 is pressed to supply electric power to the ultrasonic transducer of the transducer unit 5 to cause vibration, and transmit the vibration to the treatment portion 13 of the rod member 6. In this case, the ridges R1 and R2 of the grasping surface 73 bite the biological tissue fast, so that the biological tissue does not slip and it is possible to cut the biological tissue more quickly.

Consequently, it is possible to exhibit the function of the grasping treatment instrument 1 for the grasped biological tissue in a state where the grasping treatment instrument 1 grasps the biological tissue, and perform desired treatment. Consequently, it is possible to provide the grasping treatment instrument 1 which, when grasping the biological tissue while preventing the gap from being exposed in the back surface 37 of the jaw 31, can closely adhere the grasping surface of the grasping member 61 to the biological tissue irrespectively of a swing state of the grasping member 61.

In addition, as illustrated in FIG. 8A, at least part of the proximal end region 61b of the grasping member 61 may not be exposed to the outside at the second position by the recess 47 of the jaw 31.

As illustrated in FIGS. 3 and 4, a pair of fitting recess (fitting portions) 47a and 47b are formed on the recess 47 of the jaw 31. One pair of fitting protrusion portions (fitting portions) 74a which protrude in the width direction are formed on the back surface 74 of the grasping member 61. One pair of fitting protrusion portions (fitting portions) 74b are formed on a side surface of the proximal portion 21b of the grasping member 61. The fitting protrusion portions 74a are fitted to the fitting recesses 47a. The fitting protrusion portions 74b are fitted to the fitting recesses 47b. Consequently, the grasping member 61 is swingable around the second rotary axis S2 with respect to the jaw 31, yet is prevented from rattling in the width direction pivotally around the second rotary axis S2.

The grasping treatment instrument 1 according to the present embodiment is used to open the jaw 31 in a state where the jaw 31 is closed with respect to the rod member 6, and separate a blood vessel from a biological tissue, for example. For example, the back surface 27 of the treatment portion 13 of the rod member 6 and the back surface 37 of the jaw 31 are configured to separate the blood vessel from the biological tissue. The back surface 74 of the grasping member 61 maintains a state where back surface 74 of the grasping member 61 is disposed in the recess 47 of the jaw 31, and the back surface 37 of the jaw 31 is formed smoothly without a step. Consequently, it is possible to prevent the biological tissue and/or the blood vessel from being hooked on the back surface 37 of the jaw 31. Furthermore, rattling is prevented and a small gap is maintained between the first rim 46a of the jaw 31 and the first ridge R1 of the grasping member 61 and between the second rim 46b of the jaw 31 and the second ridge R2 of the grasping member 61. Consequently, for example, it is possible to prevent the biological tissue from entering between the first rim 46a of the jaw 31 and the first ridge R1 of the grasping member 61 and between the second rim 46b of the jaw 31 and the second ridge R2 of the grasping member 61.

The present embodiment has described an example where ultrasonic vibration is used to cut and treat a biological tissue. However, the grasping member main body 66 has conductivity, and therefore one of the inclined surfaces 71a and 71b of the grasping surface 73 can be used as an electrode. Furthermore, the treatment portion 13 of the rod member 6 can be used as the other electrode. In this case, the grasping treatment instrument 1 can be used as a bipolar high frequency treatment instrument. Particularly, the ridges R1 and R2 of the grasping surface 73 bite the biological tissue fast, so that it is possible to naturally prevent the biological tissue from slipping and reliably place the inclined surfaces 71a and 71b of the grasping surface 73 of the grasping member main body 66 having the conductivity in contact with the biological tissue. Consequently, when the grasping treatment instrument 1 is used as the bipolar high frequency treatment instrument, it is possible to reliably conduct a high frequency current to, for example, a blood vessel placed in contact with the treatment portion 13 of the rod member 6 and the inclined surfaces 71a and 71b of the grasping surface 73, and stem the blood vessel. Furthermore, when the grasping treatment instrument 1 is used as the bipolar high frequency treatment instrument and the ultrasonic transducer of the transducer unit 5 is driven, it is possible to cut the blood vessel while stemming the blood vessel. Consequently, when the grasping treatment instrument 1 is used as the bipolar high frequency treatment instrument and as the ultrasonic treatment instrument, it is possible to reliably conduct the high frequency current to the blood vessel, make blood vessel stemming capability good and cut the stemmed blood vessel more quickly.

In addition, when the grasping treatment instrument 1 is used as the bipolar high frequency treatment instrument, it is possible to reliably coagulate the biological tissue. Furthermore, when the grasping treatment instrument 1 is used as the bipolar high frequency treatment instrument and as the ultrasonic treatment instrument, it is possible to reliably conduct the high frequency current to the biological tissue, make coagulation capability good and cut the coagulated biological tissue more quickly.

Figure 5F:
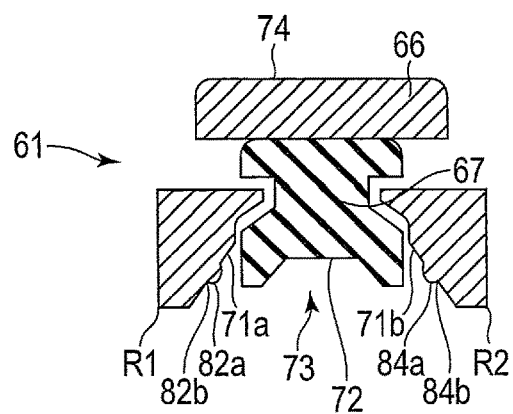
FIG. 5F illustrates a modified example of the cross-sectional view along the 5E-5E line of the grasping member in FIG. 5A.

In addition, the present embodiment has described an example where the ridges R1 and R2 are formed on an outermost rim of the grasping member 61, the first ridge R1 includes the first tooth tip regions 82a and the first recessed regions 82b and the second ridge R2 includes the second tooth tip region 84a and the second recessed regions 84b. In addition, as illustrated in FIG. 5F, the first ridge R1, the first tooth tip regions 82a and the first recessed regions 82b may be disposed at different positions. In this case, the first tooth tip regions 82a and the first recessed regions 82b are on an inner side in the width direction of the first ridge R1, and can bite the biological tissue faster than the first ridge R1. That is, the first ridge R1 is defined as, for example, a contact region with respect to the biological tissue. Similarly, the second ridge R2, the second tooth tip regions 84a and the second recessed regions 84b may be disposed at different positions. In this case, the second tooth tip regions 84a and the second recessed regions 84b are on an inner side in the width direction of the second ridge R2, and can bite the biological tissue faster than the second ridge R2. That is, the second ridge R2 is defined as, for example, a contact region with respect to the biological tissue.

Figure 9:
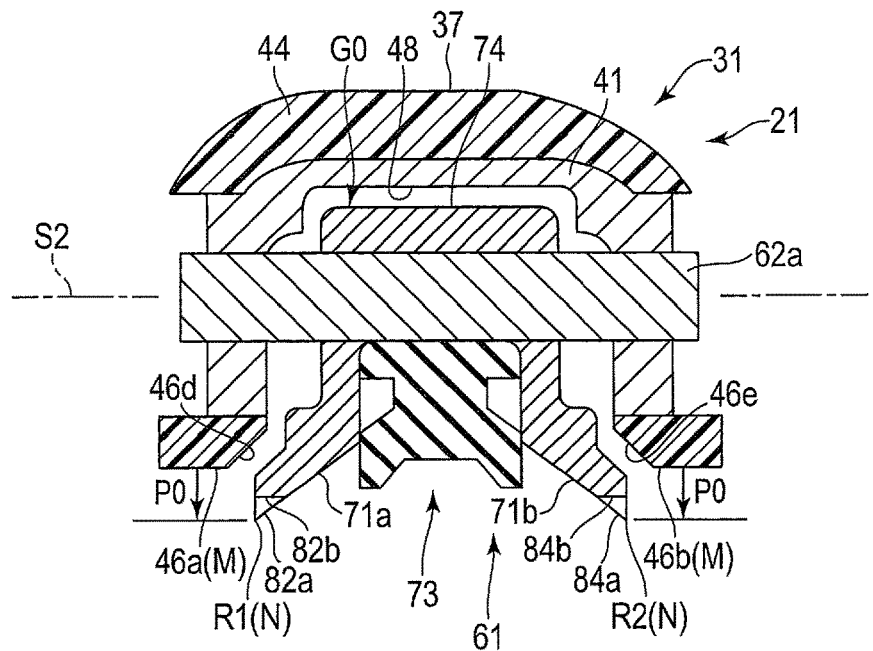
FIG. 9 illustrates a modified example of the cross-sectional view along the 6B-6B line of the grasping piece in FIG. 6A.
Figure 10:
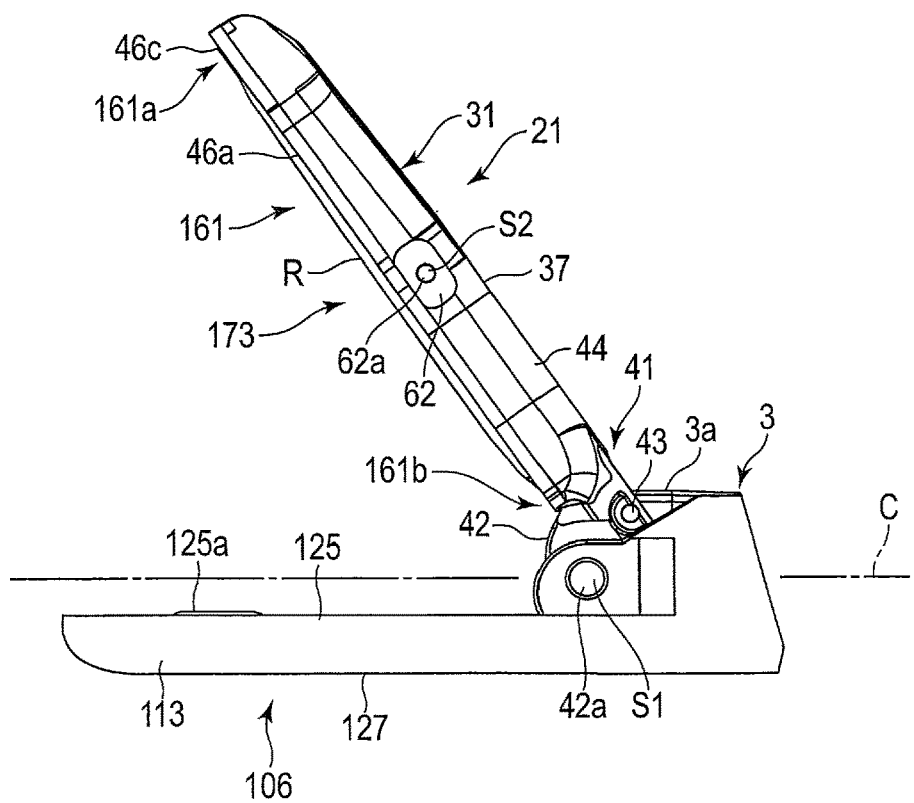
FIG. 10 is a schematic side view illustrating an end effector of a grasping treatment instrument according to the second embodiment.
Figure 11C:
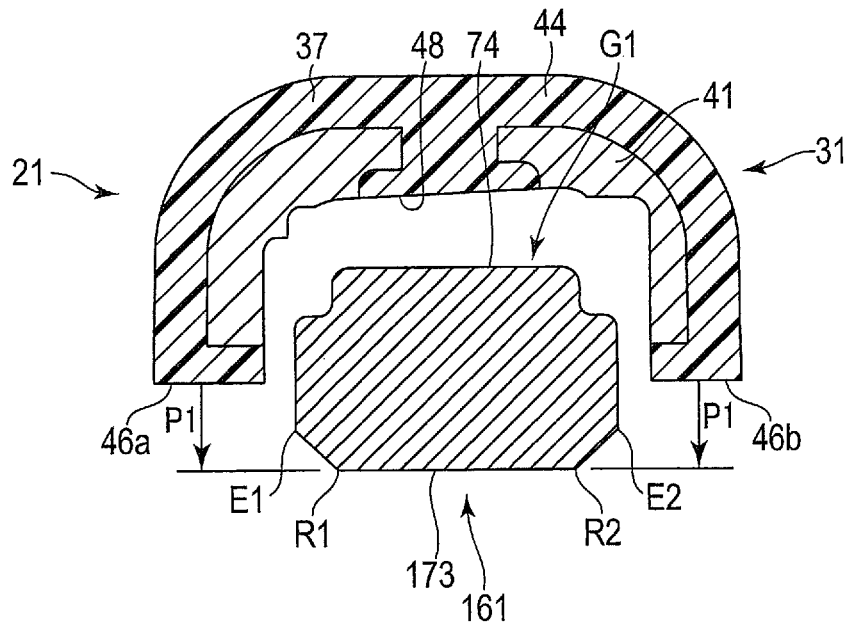
FIG. 11C is a cross-sectional view along an 11C-11C line of the grasping piece in FIG. 11A.
Figure 11D:
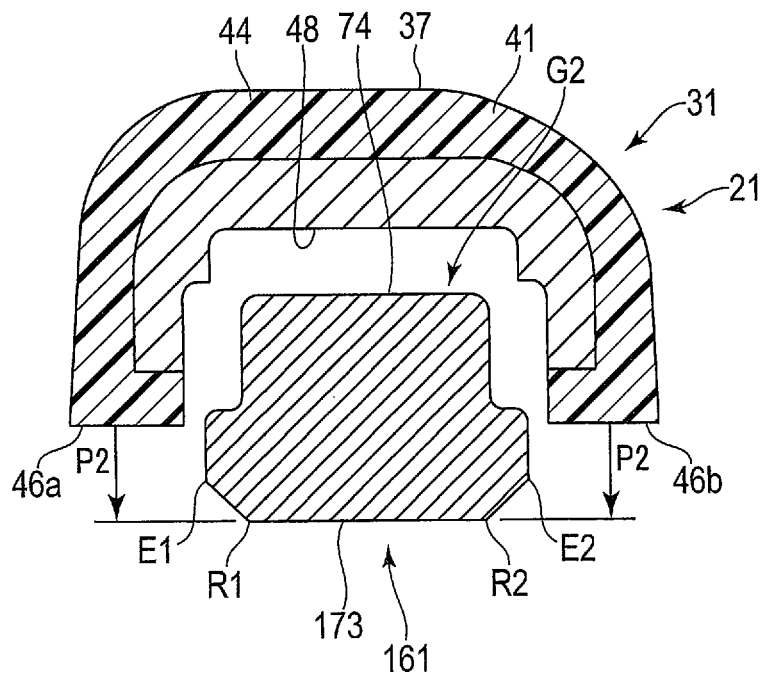
FIG. 11D is a cross-sectional view along an 11D-11D line of the grasping piece in FIG. 11A.

Furthermore, it is also preferable that the jaw 31 of the grasping piece 21 and the grasping member 61 are formed as illustrated in FIG. 9. The ridges R1 and R2 of the grasping member 61 illustrated in FIG. 9 are made thicker in the width direction of the ridges R1 and R2 of the grasping member 61 in the example illustrated in FIG. 6B. Consequently, when the grasping member 61 illustrated in FIG. 9 is used, it is possible to increase the contact area with respect to the biological tissue compared to a case where the grasping member 61 illustrated in FIG. 6B is used. On the other hand, the first rim 46a and the second rim 46b of the jaw 31 illustrated in FIG. 9 are made thinner than the first rim 46a and the second rim 46b of the jaw 31 in the example illustrated in FIG. 6B. The first rim 46a and the second rim 46b of the jaw 31 illustrated in FIG. 9 have inclined surfaces 46d and 46e which become thinner from the outer side to the inner side. These inclined surfaces 46d and 46e can prevent the first rim 46a and the second rim 46b of the jaw 31 from blocking motions of the ridges R1 and R2 of the grasping member 61 in the example illustrated in FIG. 9, too. More specifically, in the example illustrated in FIG. 9, at the first position illustrated in FIG. 7A, the back surface 74 of the grasping member 61 can be placed in contact with the bottom surface 48 of the recess 47 at a position on the distal side of the second rotary axis S2. At the second position illustrated in FIG. 8A, the back surface 74 of the grasping member 61 can be placed in contact with the bottom surface 48 of the recess 47 at the position on the proximal side of the second rotary axis S2.

Second Embodiment

Next, the second embodiment will be described with reference to FIGS. 10 to 13. The present embodiment is a modified example of the first embodiment, members which are the same members as or have the same functions as the members described in the first embodiment will be assigned the same reference numerals as much as possible, and detailed description thereof will be omitted.

An example where a grasping treatment instrument 1 according to the present embodiment does not use ultrasonic vibration and performs treatment such as cauterization of a biological tissue by using, for example, high frequency energy will be described. The grasping treatment instrument 1 illustrated in FIG. 10 uses a second grasping piece 106 instead of a rod member 6 described in the first embodiment. A treatment portion 113 of the second grasping piece 106 includes an electrode (grasping region) 125 as a treatment surface. A projection portion 125a having an electrical insulation property is fixed to the electrode 125.

A grasping member 161 of a treatment piece 21 illustrated in FIGS. 11A to 11D includes a grasping surface 173. The grasping surface 173 is formed as a high frequency electrode. The grasping surface 173 does not need to be formed as an inclined surface. Furthermore, a pad member 67 does not need to be provided. In addition, any slip stopper (not illustrated) such as a recess/protrusion shape for preventing slip when a biological tissue is grasped is optimally formed on the grasping surface 173.

Outer edges E1 and E2 which continue to the side surface are formed on the outer side in a width direction of the grasping surface 173 of the grasping member 161.

The grasping surface 173 of the grasping member 161 includes a ridge R (R1 and R2) which grasps the biological tissue. The ridge R includes, for example, the first ridge R1 which is close to a first rim 46a and is formed in parallel to the first rim 46a, and the second ridge R2 which is close to a second rim 46b and is formed in parallel to the second rim 46b. In this regard, the first ridge R1 is adjacent on the inner side of the first rim 46a, and is formed on the inner side of an outermost position (outer edge E1) in the width direction. Thus, it is preferable that the first ridge R1 is apart in the width direction from the first rim 46a. In this regard, the second ridge R2 is adjacent on the inner side of the second rim 46b, and is formed on the inner side of an outermost position (outer edge E2) in the width direction. Thus, it is preferable that the second ridge R2 is apart in the width direction from the second rim 46b.

In this regard, a region 161a on a distal side of a distal end 81a of the first ridge R1 and a distal end 83a of the second ridge R2, and the electrode 125 of the second grasping piece 106 are used to pinch (grasp) the biological tissue at a distal portion of an end effector 10. Hence, it is preferable that the distal end 81a of the first ridge R1 and the distal end 83a of the second ridge R2 are on the proximal side of the distalmost end region (distal portion) 161a of the grasping member 161. A region 161b on the proximal side of a proximal end 81b of the first ridge R1 and a proximal end 83b of the second ridge R2 is less likely to be used to grasp the biological tissue. Hence, it is preferable that the proximal end 81b of the first ridge R1 and the proximal end 83b of the second ridge R2 are on the distal side of a proximalmost end region (proximal portion) 161b of the grasping member 161. Hence, rims (first ridge R1 and the second ridge R2) which are in contact with the biological tissue are formed in most regions from the distal end to the proximal end of the grasping member 161, yet do not need to be formed in the entire region.

Figure 12:
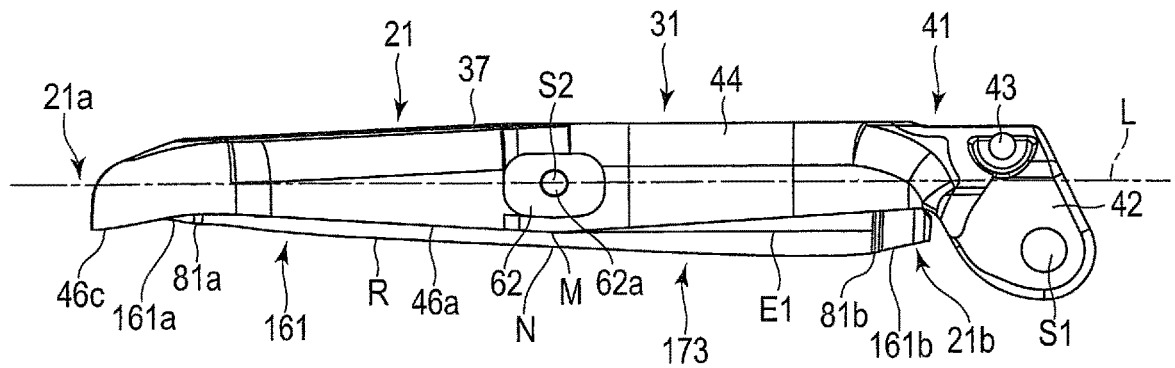
FIG. 12 is a schematic view illustrating a first position at which a back surface of the grasping member is placed in contact with a bottom surface of a recess of the jaw of the grasping piece of the grasping treatment instrument according to the second embodiment at a position on a distal side of a second rotary axis.
Figure 13:
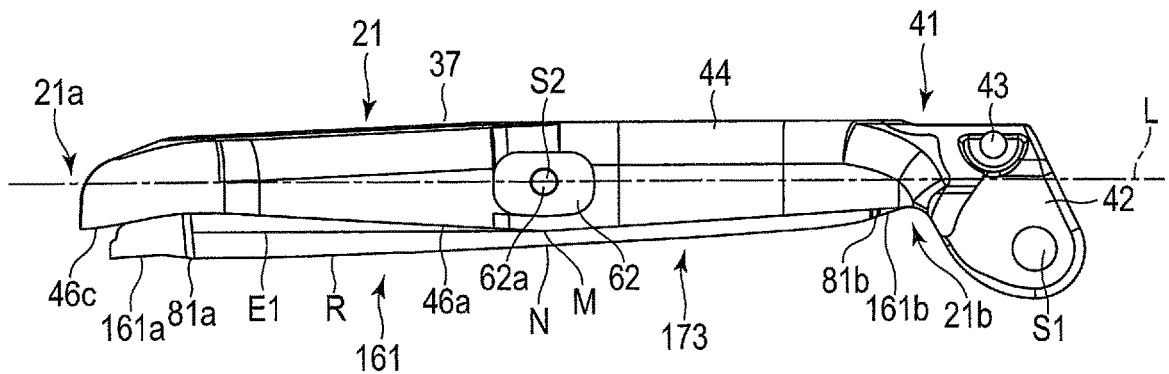
FIG. 13 is a schematic view illustrating a second position at which the back surface of the grasping member is placed in contact with a position on a proximal side of the second rotary axis on the bottom surface of the recess of the jaw of the grasping piece of the grasping treatment instrument according to the second embodiment.

In the present embodiment, at each one of a neutral position illustrated in FIG. 11A, a first position illustrated in FIG. 12 and a second position illustrated in FIG. 13, the entire region from the distal end 81a to the proximal end 81b of the first ridge R1 protrudes from the first rim 46a. Consequently, when the grasping member 161 which can swing with respect to a jaw 31 is used to grasp the biological tissue, it is possible to reliably place the first ridge R1 and the second ridge R2 in contact with the biological tissue at any swing position. By applying high frequency energy to the biological tissue between the electrode 125 and a grasping surface 173 which is in contact with the first ridge R1 and the second ridge R2 in this state, it is possible to cauterize the grasped biological tissue. Consequently, it is possible to exhibit the function of the grasping treatment instrument 1 for the grasped biological tissue in a state where the grasping treatment instrument 1 grasps the biological tissue, and perform desired treatment. Consequently, it is possible to provide the grasping treatment instrument 1 which, when grasping the biological tissue while preventing a gap from being exposed in a back surface 37 of the jaw 31, can place the grasping surface 173 of the grasping member 161 in contact with the biological tissue irrespectively of a swing state of the grasping member 161.

When the grasping piece 21 is closed with respect to the second grasping piece 106, the projection portion 125*a* comes into contact with the grasping surface 173 of the grasping member 161 even in any state of the grasping member 161 with respect to the jaw 31. Hence, the electrode 125 is prevented from coming into contact with the grasping surface 173 of the grasping member 161.

In addition, as illustrated in FIGS. 12 and 13, a coupling portion 46*c* of the jaw 31 exposes at least part of the distal end region 161*a* of the grasping member 161 to the outside at the first position and the second position. Furthermore, as illustrated in FIG. 13, at least part of the proximal end region 161*b* of the grasping member 161 may not be exposed to the outside at the second position by a recess 47 of the jaw 31.

Third Embodiment

Next, the third embodiment will be described with reference to FIGS. 14A to 14D. The present embodiment is a modified example of the first and second embodiments, members which are the same members as or have the same functions as the members described in the first and second embodiments will be assigned the same reference numerals as much as possible, and detailed description thereof will be omitted.

An example where a grasping treatment instrument 1 illustrated in FIGS. 14A to 14D treats the biological tissue by heat transfer of a heater 267 will be described. A grasping member 261 is formed by a good heat transfer material. Furthermore, the grasping member 216 includes the heater 267. In this regard, unlike the second embodiment, ridges R1 and R2 are located on an outermost side in a width direction.

Figure 14A:
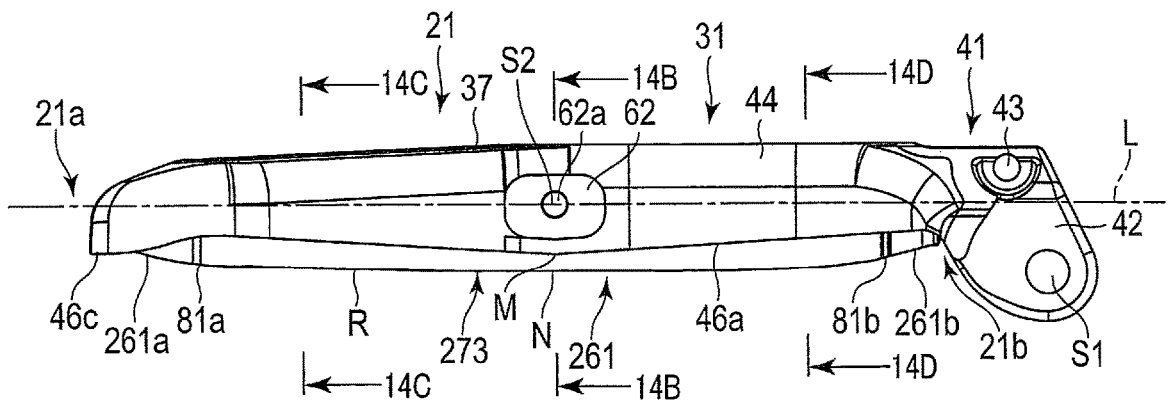
FIG. 14A is a schematic view illustrating a neutral state where the grasping member is disposed swingably along a longitudinal axis of a jaw of a grasping piece of a grasping treatment instrument according to the third embodiment.

Similar to the above-described first and second embodiments, in the present embodiment, at any one of a neutral position illustrated in FIG. 14A, a first position (not illustrated) and a second position (not illustrated), an entire region from a distal end 81*a* to a proximal end 81*b* of the first ridge R1 protrudes from a first rim 46*a*. Consequently, when the grasping member 261 which can swing with respect to a jaw 31 is used to grasp the biological tissue, it is possible to reliably place the first ridge R1 and the second ridge R2 in contact with the biological tissue at any swing position.

When the heater 267 is heated in this state, heat is transmitted to a grasping surface 273. Consequently, the heater 267 transmits heat to the grasped biological tissue through the grasping surface 273, so that the grasping treatment instrument 1 according to the present embodiment can cauterize the grasped biological tissue. Consequently, it is possible to exhibit the function of the grasping treatment instrument 1 for the grasped biological tissue in a state where the grasping treatment instrument 1 grasps the biological tissue, and perform desired treatment.

Here, the example where the biological tissue is treated by heat transfer of the heater 267 has been described. However, it is naturally optimal to use the grasping surface 273 as a high frequency electrode.

Fourth Embodiment

Next, the fourth embodiment will be described with reference to FIG. 15. The present embodiment is a modified example of the first to third embodiments, members which are the same members as or have the same functions as the members described in the first to third embodiments will be assigned the same reference numerals as much as possible, and detailed description thereof will be omitted.

According to the present embodiment, a rim 346*a* of a jaw 31 illustrated in FIG. 15 is formed in parallel to a longitudinal axis L at a neutral position unlike the first to third embodiments. Furthermore, according to the present embodiment, a ridge R of a grasping member 61 is not parallel or substantially parallel to the longitudinal axis L at the neutral position. In this regard, the ridge R of the grasping member 61 slightly inclines with respect to the longitudinal axis L. A minimum distance T0 between the ridge R of the grasping member 61 and the longitudinal axis L is formed at a position N near a second rotary axis S2. At any position from the position N near the second rotary axis S2 to a distal portion 21*a*, a distance T1 between the ridge R of the grasping member 61 and the longitudinal axis L is longer than the distance T0 (T1>T0). At any position from the position N near the second rotary axis S2 to a proximal portion 21*b*, a distance T2 between the ridge R of the grasping member 61 and the longitudinal axis L is longer than the distance T0 (T2>T0). Furthermore, the distance T1 between the ridge R of the grasping member 61 and the longitudinal axis L gradually becomes longer from the position N near the second rotary axis S2 to the distal portion 21*a*. The distance T2 between the ridge R of the grasping member 61 and the longitudinal axis L gradually becomes longer from the position N near the second rotary axis S2 to the proximal portion 21*b*. Hence, at the neutral position, the rim 346*a* becomes gradually apart from the ridge R of the grasping member 61 from a vicinity M of the second rotary axis S2 toward the distal portion 21*a* and the proximal portion 21*b*. Although not illustrated, it is preferable that the another rim of the jaw 31 is formed similar to the above rim 346*a*.

Furthermore, the ridge R of the grasping member 61 protrudes from the rim 346*a* in a region between a distal end 81*a* and a proximal end 81*b* not only at the neutral position illustrated in FIG. 15 but also at the first position and the second position (P0>0, P1>G1>0 and P2>G2>0). Consequently, when the grasping member 61 which can swing with respect to the jaw 31 is used to grasp the biological tissue, it is possible to reliably place the ridge R of the grasping member 61 in contact with the biological tissue.

Unlike the first to third embodiments, the rim 346*a* of the cover 44 of the jaw 31 according to the present embodiment is formed straight. In this case, the rim 346*a* becomes apart from the ridge R of the grasping member 61 from (the position N near) the second rotary axis S2 to each of the distal portion 21*a* and the proximal portion 21*b*. Furthermore, even in this case, the ridge R of the grasping member 61 protrudes from the rim 346*a* toward a side opposite to a direction traveling toward a bottom surface 48 of a recess 47 in the region between the distal portion 21a and the proximal portion 21b of the jaw 31 in any turning range between the first position and the second position, and reliably come into contact with the biological tissue. Thus, as long as the rim of the jaw 31 and the ridge R of the grasping member 61 have shapes which become gradually apart from the second rotary axis S2 toward each of the distal portion 21a and the proximal portion 21b, the shapes of the rim of the jaw 31 and the ridge R of the grasping member 61 can be variously changed. Although not illustrated, as long as the rim of the jaw 31 and the ridge R of the grasping member 61 have shapes which become gradually apart from the second rotary axis S2 toward each of the distal portion 21a and the proximal portion 21b, both of the rim of the jaw 31 and the ridge R of the grasping member 61 may not be straight.

Examples where the grasping treatment instrument 1 according to the first to fourth embodiments treats biological tissues by using various types of energy have been described. However, it is naturally optimal to be used as a forceps which does not use energy.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A grasping treatment instrument comprising:
   a jaw including:
      a first rim and a second rim juxtaposed to a longitudinal axis of the jaw extending in a direction between a distal portion and a proximal portion of the jaw, the first rim being separated from the second rim in a width direction,
      a recess with a bottom surface formed between the first rim and the second rim, and
      a connection portion that connects the first rim and the second rim, the connection portion protruding from the bottom surface of the recess in a direction intersecting with the longitudinal axis and the width direction,
      the jaw being configured to be turnable around a first rotary axis intersecting with the longitudinal axis at the proximal portion; and
   a grasping member including a distal end region, proximal end region, and a ridge which is formed between the distal end region and the proximal end region of the grasping member, a distal end and lateral sides of the distal end region of the grasping member being surrounded by the connection portion, the ridge including a distal end and a proximal end, the distal end being positioned at a proximal side with respect to the distal end region of the grasping member, and the proximal end being positioned at a distal side with respect to the proximal end region of the grasping member,
      the grasping member being supported by the recess of the jaw such that the grasping member is turnable with respect to the jaw around a second rotary axis that is at a position between the distal end and the proximal end of the ridge on a distal side of the first rotary axis, the grasping member being configured to be turnable between:
         a first position at which the grasping member is in contact with the bottom surface of the recess at a position on a distal side of the second rotary axis, and
         a second position at which the grasping member is in contact with the bottom surface of the recess at a position on a proximal side of the second rotary axis,
      wherein:
         when the grasping member is positioned at the first position, a component of the ridge between the second rotary axis and the distal end of the ridge protrudes to an opposite side from the bottom surface of the recess with respect to the first rim and the second rim, and
         when the grasping member is positioned at the second position, a component of the ridge between the second rotary axis and the proximal end of the ridge protrudes to the opposite side from the bottom surface of the recess with respect to the first rim and the second rim.

2. The grasping treatment instrument according to claim 1, wherein, in a state in which the grasping member is in any position in a range between the first position and the second position, the ridge includes components between the distal end and the proximal end of the ridge that protrude to the opposite side from the bottom surface of the recess with respect to the first rim and the second rim.

3. The grasping treatment instrument according to claim 1, wherein, in a state in which the grasping member is in a neutral position, which is an intermediate position between the first position and the second position, the first rim and the second rim of the jaw extend in directions from the second rotary axis toward each of the distal portion and the proximal portion of the jaw so as to be inclined in directions away from the ridge of the grasping member.

4. The grasping treatment instrument according to claim 1, wherein the jaw includes a cover having an electrical insulation property on at least part of an outer circumferential surface on a side opposite to the bottom surface of the recess.

5. The grasping treatment instrument according to claim 4, wherein the first rim and the second rim of the jaw are formed as part of the cover.

6. The grasping treatment instrument according to claim 1, wherein the grasping member is configured as an electrode having conductivity.

7. The grasping treatment instrument according to claim 1, wherein:
   the grasping member includes a grasping surface with the ridge, and
   the grasping treatment instrument includes a grasping region which faces the grasping surface and which is configured to grasp a biological tissue between the grasping region and the grasping surface.

8. The grasping treatment instrument according to claim 1, wherein:
   the ridge includes a plurality of first tooth tip regions between the distal end and the proximal end of the ridge, and
   all of the plurality of first tooth tip regions protrude to the opposite side from the bottom surface of the recess with respect to the first rim and the second rim, in a state in which the grasping member is in any position in a range between the first position and the second position.

9. The grasping treatment instrument according to claim 1, wherein the ridge includes:

a first tooth tip ridgeline adjacent to the first rim of the jaw, and
a second tooth tip ridgeline adjacent to the second rim of the jaw.

10. The grasping treatment instrument according to claim 9, wherein:
the grasping member includes a pad member having an electrical insulation property, the pad member being formed between the first tooth tip ridgeline and the second tooth tip ridgeline, the pad member facing a grasping region of a treatment portion,
the pad member includes:
a facing surface which faces the grasping region, and
a pad inclined surface which is inclined toward the grasping region in a direction toward the distal side along the longitudinal axis, and
the pad inclined surface protrudes to the opposite side from the bottom surface of the recess with respect to the first rim and the second rim.

11. The grasping treatment instrument according to claim 9, wherein:
the first tooth tip ridgeline includes:
a plurality of first tooth tip regions which protrude toward the first rim and are formed between the distal end and the proximal end of the grasping member, and
a first recessed region which is formed between the first tooth tip regions and which is recessed toward a back surface of the grasping member compared to the first tooth tip regions, and
the second tooth tip ridgeline includes:
a plurality of second tooth tip regions which protrude toward the second rim and are formed between the distal end and the proximal end of the grasping member, and
a second recessed region which is formed between the second tooth tip regions and which is recessed toward the back surface of the grasping member compared to the second tooth tip regions.

12. The grasping treatment instrument according to claim 9, wherein:
the grasping member includes a pad member disposed between the first tooth tip ridgeline and the second tooth tip ridgeline, the pad member having an electrical insulation property, and
the grasping treatment instrument includes a grasping region which faces the pad member and which is configured to grasp a biological tissue between the grasping region and the pad member.

13. The grasping treatment instrument according to claim 12, wherein the grasping treatment instrument is configured to transmit ultrasonic vibration to the grasping region.

14. The grasping treatment instrument according to claim 9, wherein:
the grasping member includes a grasping surface with the ridge,
the grasping treatment instrument includes a grasping region which faces the grasping surface and which is configured to grasp a biological tissue between the grasping region and the grasping surface, and
the distal end region of the grasping member is between a distal end of the first tooth tip ridgeline and a distal end of the second tooth tip ridgeline, the distal end region being configured to grasp the biological tissue in cooperation with the grasping region.

15. The grasping treatment instrument according to claim 14, wherein:

the connection portion is configured to protect a distal side of the distal end region of the grasping member at a distal side of the first rim and the second rim of the jaw, and
the connection portion exposes at least part of the distal end region to an outside at the first position and the second position.

16. The grasping treatment instrument according to claim 9, wherein:
the proximal end region of the grasping member is on a proximal side of the first tooth tip ridgeline and the second tooth tip ridgeline, and
at least part of the proximal end region is not exposed to an outside at the second position by the recess of the jaw.

17. A grasping treatment instrument comprising:
a jaw including a distal portion and a proximal portion and extending along a longitudinal axis, the jaw being configured to rotate around a first rotary axis relative to a shaft, the first rotary axis being disposed at the proximal portion and intersecting with the longitudinal axis, the jaw including:
a first rim extending from the distal portion to the proximal portion along the longitudinal axis;
a second rim extending from the distal portion to the proximal portion along the longitudinal axis, the second rim being apart from the first rim;
a connection portion disposed at the distal portion, the connection portion connecting the first rim and the second rim; and
a bottom surface extending from the distal portion to the proximal portion in the longitudinal axis, the bottom surface being formed between the first rim and the second rim; and
a grasping member including a distal region and a proximal region, a distal end and lateral sides of the distal region being surrounded by the connection portion, the grasping member being configured to rotate around a second rotary axis relative to the jaw between a first position and a second position, the second rotary axis being positioned between the distal region and the proximal region and being positioned distal of the first rotary axis, the grasping member including:
a first ridge extending from the distal region to the proximal region and being adjacent to the first rim, the first ridge including a first part disposed at the distal region and a second part disposed at the proximal region; and
a second ridge extending from the distal region to the proximal region and being adjacent to the second rim, the second ridge including a first part disposed at the distal region and a second part disposed at the proximal region;
wherein in the first position, the distal region contacts the bottom surface, the first part of the first ridge protrudes outside beyond the first rim, and the first part of the second ridge protrudes outside beyond the second rim, and
wherein in the second position, the proximal region contacts the bottom surface, the second part of the first ridge protrudes outside beyond the first rim, and the second part of the second ridge protrudes outside beyond the second rim.

18. The grasping treatment instrument according to claim 17, wherein:

the grasping member includes an inclined surface inclined in a direction intersecting with the longitudinal axis, the inclined surface being positioned at the distal region.

19. The grasping treatment instrument according to claim 17, wherein:
the first rim includes a first portion and a second portion, the first portion of the first rim is disposed distal of the second rotary axis, and the second portion of the first rim is disposed proximal of the second rotary axis,
a distance from the longitudinal axis of the jaw intersecting with the second rotary axis to the first portion of the first rim is a first distance, a distance from the longitudinal axis of the jaw to the second portion of the first rim is a second distance, and a distance from the second rotary axis to the first rim is a third distance,
the first distance is shorter than the third distance,
the second distance is shorter than the third distance,
the second rim includes a first portion and a second portion, the first portion of the second rim is disposed distal of the second rotary axis, and the second portion of the second rim is disposed proximal of the second rotary axis,
a distance from the longitudinal axis of the jaw intersecting with the second rotary axis to the first portion of the second rim is a fourth distance, a distance from the longitudinal axis of the jaw to the second portion of the second rim is a fifth distance, and a distance from the second rotary axis to the second rim is a sixth distance,
the fourth distance is shorter than the sixth distance, and
the fifth distance is shorter than the sixth distance.

* * * * *